US 8,673,824 B2

(12) United States Patent
Neri et al.

(10) Patent No.: US 8,673,824 B2
(45) Date of Patent: Mar. 18, 2014

(54) ENCODED SELF-ASSEMBLING CHEMICAL LIBRARIES (ESACHEL)

(75) Inventors: Dario Neri, Zurich (CH); Samu Melkko, Zurich (CH)

(73) Assignee: Eidgenoessische Technische Hochschule Zürich (CH)

( * ) Notice: Subject to any disclaimer, the term of this patent is extended or adjusted under 35 U.S.C. 154(b) by 609 days.

(21) Appl. No.: 12/613,475

(22) Filed: Nov. 5, 2009

(65) Prior Publication Data

US 2011/0319278 A1      Dec. 29, 2011

Related U.S. Application Data

(60) Division of application No. 12/555,707, filed on Sep. 8, 2009, now Pat. No. 8,642,514, which is a continuation of application No. 10/382,107, filed on Mar. 5, 2003, now abandoned, said application No. 12/555,707 is a continuation-in-part of application No. 10/507,140, filed as application No. PCT/EP02/04153 on Apr. 15, 2002, now abandoned.

(60) Provisional application No. 60/362,599, filed on Mar. 8, 2002.

(51) Int. Cl.
   *C40B 40/06*       (2006.01)
   *C40B 30/04*       (2006.01)
   *C07H 21/00*       (2006.01)
   *C07H 21/04*       (2006.01)

(52) U.S. Cl.
   USPC ............... 506/16; 506/9; 536/22.1; 536/23.1

(58) Field of Classification Search
   USPC ............................. 506/9, 16; 536/22.1, 23.1
   See application file for complete search history.

(56) References Cited

U.S. PATENT DOCUMENTS

| 5,573,905 A | 11/1996 | Lerner et al. |
| 5,723,598 A | 3/1998 | Lerner et al. |

(Continued)

FOREIGN PATENT DOCUMENTS

| AU | 718917 B2 | 2/1997 |
| AU | 757912 B2 | 4/1997 |

(Continued)

OTHER PUBLICATIONS

Liu et al., Methods in Enzymology, 2000, vol. 318, pp. 268-293.*

(Continued)

*Primary Examiner* — Christopher M Babic
*Assistant Examiner* — Jeremy C Flinders
(74) *Attorney, Agent, or Firm* — Kilpatrick Townsend & Stockton LLP

(57) ABSTRACT

The invention provides a chemical compound comprising a chemical moiety (p) capable of performing a binding interaction with a target molecule, and an oligonucleotide (b) or functional analogue thereof. The oligonucleotide (b) or functional analogue comprises at least one self-assembly sequence (b1) capable of performing a combination reaction with at least one self-assembly sequence (b1') of a complementary oligonucleotide or functional analogue bound to another chemical compound comprising a chemical moiety (q). In some embodiments, the chemical compound comprises a coding sequence (b1) coding for the identification of the chemical moiety (p) and further comprises at least one self-assembly moiety (m) capable of performing a combination reaction with at least one self-assembly moiety (m') of a similar chemical compound comprising a chemical moiety (q). The invention also provides corresponding libraries of chemical compounds as well as methods of biopanning of for target molecules and of identifying such targets.

17 Claims, 13 Drawing Sheets

(56) References Cited

U.S. PATENT DOCUMENTS

Figure 1:
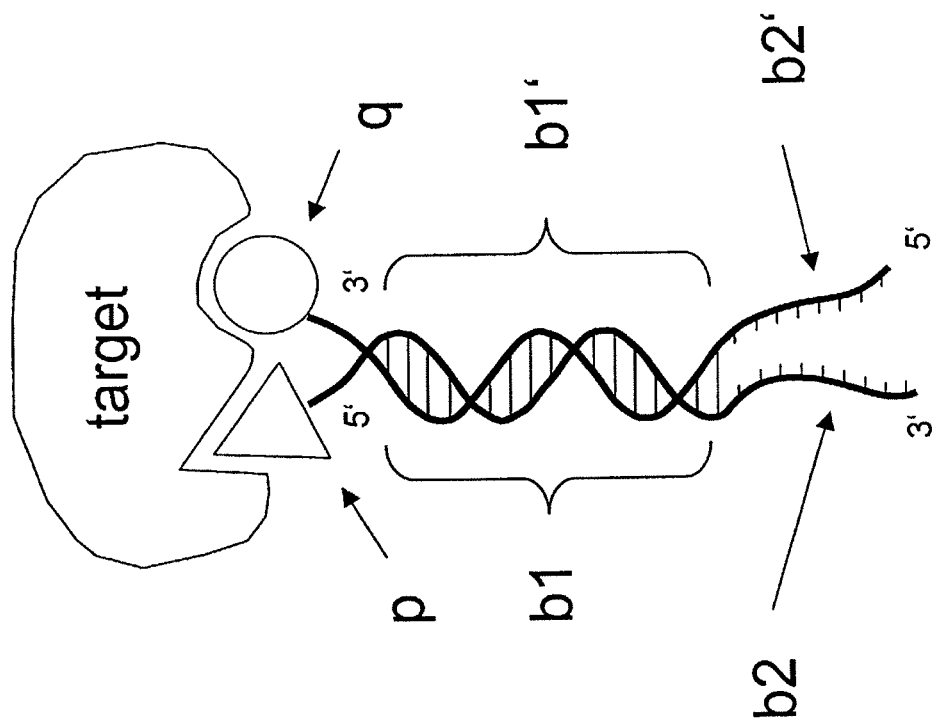

| | | | |
|---|---|---|---|
| 6,060,596 | A | 5/2000 | Lerner et al. |
| 6,087,103 | A | 7/2000 | Burmer |
| 2003/0113738 | A1* | 6/2003 | Liu et al. .......................... 435/6 |
| 2003/0148335 | A1 | 8/2003 | Shen et al. |
| 2003/0157505 | A1 | 8/2003 | Miculka et al. |
| 2004/0058373 | A1 | 3/2004 | Wnkler et al. |

FOREIGN PATENT DOCUMENTS

| | | |
|---|---|---|
| CA | 2 303 086 A1 | 4/1999 |
| DE | 19619373 A1 | 11/1997 |
| DE | 19741716 A1 | 3/1999 |
| WO | WO 00/23458 A1 | 4/2000 |
| WO | WO 03/076943 A1 | 9/2003 |

OTHER PUBLICATIONS

Jamieson et al., Chemical Reviews, 1999, 99:2467-2498.*
Ghosh et al., Bioconjugate Chem., 1990, 1(1):71-76.*
Tsoi et al., Langmuir, 2000, 16:6590-6.*
Office Action dated Oct. 3, 2011 issued in related U.S. Appl. No. 12/555,707.
Brown et al. "Exploring the new world of the genome with DNA microarrays," Nature Genetics, 1999, 21: 33-37.
Boder, E.T. et al., "Yeast Surface Display for Screening Combinatorial Polypeptide Libraries," *Nature Biotechnology*, Jun. 1997, vol. 15, pp. 553-557.
Böhm, H-J. et al., "Structure-Based Library Design: Molecular Modelling Merges With Combinatorial Chemistry," *Current Opinions in Chemical Biology*, 2000, vol. 4, pp. 283-286.
Brenner et al., Encoded combinatorial chemistry, *Proc Natl Acad Sci USA*, 1992, vol. 89:5381-83.
Brody, E.N. et al., "Aptamers as Therapeutic and Diagnostic Agents," *Reviews in Molecular Biotechnology*, 2000, vol. 74, pp. 5-13.
Chen, G. et al., "Isolation of High-Affinity Ligand-Binding Proteins by Periplasmic Expression With Cytometric Screening (PECS)," *Nature Biotechnology*, Jun. 2001, vol. 19, pp. 537-542.
Cull, M.G. et al., "Screening for Receptor Ligands Using Large Libraries of Peptides Linked to the C Terminus of the *lac* Repressor," *Proc. Natl. Acad. Sci. USA*, Mar. 1992, vol. 89, pp. 1865-1869.
Desidero, A. et al., "A Semi-Synthetic Repertoire of Intrinsically Stable Antibody Fragments Derived From a Single-Framework Scaffold," *J. Mol. Biol.*, 2001, vol. 310, pp. 603-615.
Distefano, M.D. et al., "Energetics of Cooperative Binding of Oligonucleotides With Discrete Dimerization Domains to DNA by Triple Helix Formation," *Proc. Natl. Acad. Sci. USA*, Feb. 1993, vol. 90, pp. 1179-1183.
Drews, J., "Drug Discovery: A Historical Perspective," *Science*, Mar. 17, 2000, vol. 287, pp. 1960-1964.
Dumelin, C.E. et al., "DNA-Encoded Chemical Libraries," *QSAR Comb. Sci.*, 2006, vol. 25, pp. 1081-1087.
Dumelin, C.E. et al., "Secretion of Streptavidin Binders From a DNA-Encoded Chemical Library," *Bioconjugate Chem.*, 2006, vol. 17, No. 2, pp. 366-370.
Giovannoni, L. et al., "Isolation of Anti-Angiogenesis Antibodies From a Large Combinatorial Repertoire by Colony Filter Screening," *Nucleic Acids Research*, 2001, vol. 29, No. 5, pp. 1-6.
*J. Biol. Chem.*, 1998, vol. 273:21769-76.
Keniry, M.A., "Quadruplex Structures in Nucleic Acids," *Nucleic Acid Sci.*, 2001, vol. 56, pp. 123-146.
Melkko, S. et al., "Encoded Self-Assembling Chemical Libraries," *Nature Biotechnology*, May 2004, vol. 22, No. 5, pp. 568-574.
Melkko, S. et al., "Lead Discovery by DNA-Encoded Chemical Libraries," *Drug Discovery Today*, Jun. 2007, vol. 12, No. 11/12, pp. 465-471.
Morgan, G.T. et al., "Researches on Residual Affinity and Coordination. Part II. Acetylacetones of Selenium and Tellurium," *J. Chem. Soc.*, 1920, vol. 117, pp. 1456-1465.
Neri, D. et al., "High-Affinity Antigen Binding by Chelating Recombinant Antibodies (CRAbs)," *J. Mol. Biol.*, 1995, vol. 246, pp. 367-373.
Otto et al., "Dynamic combinatorial chemistry," *DDT*, Jan. 2002, vol. 7:117-124.
Pellecchia, M. et al., "NMR in Drug Discovery," *Nature Reviews*, Mar. 2002, vol. 1, pp. 211-219.
Pini, A. et al., "Design and Use of Phage Display Library," *The Journal of Biological Chemistry*, Aug. 21, 1998, vol. 273, No. 34, pp. 21769-21776.
Pospisilova, et al., *Photochemistry and Photobiology*, 1998, vol. 64(4):386-390.
*Proc Natl Acad Sci USA*, 1993, vol. 90:1179-83.
Ramström, O. et al., "Drug Discovery by Dynamic Combinatorial Libraries," *Nature*, Jan. 2002, vol. 1, pp. 26-36.
Schaffitzel, C. et al., "Ribosome Display: An in Vitro Method for Selection and Evolution of Antibodies From Libraries," *Journal of Immunological Methods*, 1999, vol. 231, pp. 119-135.
Scheuermann, J. et al., "DNA-Encoded Chemical Libraries," *Journal of Biotechnology*, 2006, vol. 126, pp. 568-581.
Shuker, S.B. et al., "Discovering High-Affinity Ligands for Proteins: SAR by NMR," *Science*, Nov. 29, 1996, vol. 274. pp. 1531-1534.
Strobel, S.A. et al., "Single-Site Enzymatic Cleavage of Yeast Genomic DNA Mediated by Triple Helix Formation," *Nature*, Mar. 14, 1991, vol. 350, pp. 172-174.
Tagore, D.M. et al., "Protein Recognition and Denaturation by Self-Assembling Fragments on a DNA Quadruplex Scaffold," *Angew. Chem. Int. Ed.*, 2007, vol. 46, pp. 223-225.
Various Authors, *Issue of Biopolymers*, 2001, vol. 56:12-227.
Viti, F. et al., "Design and Use of Phage Display Libraries for the Selection of Antibodies and Enzymes," *Methods in Enzymology*, 2000, vol. 326, pp. 480-505.
Winter, G. et al., "Making Antibodies by Phage Display Technology," *Annual Review Immunol.*, 1994, vol. 12, pp. 433-455.
Lam et al., "A One-Bead One-Peptide Combinatorial Library Method for B-Cell Epitope Mapping," 1996, 9, 482-493.
Office Action in dated Mar. 1, 2012, issued in related U.S. Appl. No. 12/555,707, filed Sep. 8, 2009.

* cited by examiner

From Chu et al. (1998, Protein Sci 7 pp. 848)

IMI = iminibiotin, SA = streptavidin

ID SELF-ASSEMBLING CHEMICAL
LIBRARIES (ESACHEL)

ASSOCIATED APPLICATION DATA

This application claims priority of the U.S. Provisional Application No. 60/362,599 filed on Mar. 8, 2002 and of the international application PCT/EP 02/04153 filed on Apr. 15, 2002.

ABSTRACT

Problem to be Solved

The isolation of specific binding molecules (e.g. organic molecules) is a central problem in chemistry, biology and pharmaceutical sciences. Typically, millions of molecules have to be screened, in order to find a suitable candidate. The preparation of very large libraries of organic molecules is typically cumbersome. Furthermore, the complexity associated with the identification of specific binding molecules from a pool of candidates grows with the size of the chemical library to be screened.

Solution

In this invention, we use self-assembling libraries of organic molecules (typically forming dimers, trimers or tetramers), in which the organic molecules are linked to an oligonucleotide which mediates the self-assembly of the library and/or provides a code associated to each binding moiety. The resulting library can be very large (as it originates by the combinatorial self-assembly of smaller sub-libraries). After the capture of the desired binding specificities on the target of interest, the "binding code" can be "decoded" by a number of experimental techniques (e.g., hybridization on DNA chips or by a modified polymerase chain reaction (PCR) technique followed by sequencing).

INTRODUCTION

The isolation of specific binding molecules (e.g., organic molecules) is a central problem in chemistry, biology and pharmaceutical sciences. For example, the vast majority of the drugs approved by the U.S. Food and Drug Administration are specific binders of biological targets which fall into one of the following categories: enzymes, receptors or ion channels. The specific binding to the biological target is not per se sufficient to turn a binding molecule into a drug, as it is widely recognized that other molecular properties (such as pharmacokinetic behaviour and stability) contribute to the performance of a drug. However, the isolation of specific binders against a relevant biological target typically represents the starting point in the process which leads to a new drug [Drews J. Drug discovery: a historical perspective. Science (2000) 287:1960-1964].

The ability to rapidly generate specific binders against the biological targets of interest would be invaluable also for a variety of chemical and biological applications. For example, the specific neutralization of a particular epitope of the intracellular protein of choice may provide information on the functional role of this epitope (and consequently of this protein). In principle, the use of monoclonal antibodies specific for a given epitope may provide the same type of information [Winter G, Griffiths A D, Hawkins R E, Hoogenboom H R. Making antibodies by phage display technology. Annu Rev Immunol. (1994) 12:433-455]. However, most antibodies do not readily cross the cell membrane and have to be artificially introduced into the cell of interest. In principle, intracellular antibodies can also be expressed into target cells by targeted gene delivery (e.g., by cell transfection with DNA directing the expression of the antibody). In this case, the antibody often does not fold, as the reducing intracellular milieu does not allow the formation of disulfide bonds which often contribute in an essential manner to antibody stability [Desiderio A, Franconi R, Lopez M, Villani M E, Viti F, Chiaraluce R, Consalvi V, Neri D, Benvenuto E. A semi-synthetic repertoire of intrinsically stable antibody fragments derived from a single-framework scaffold. J Mol. Biol. (2001) 310: 603-615]. High affinity binding molecules amenable to chemical synthesis may provide a valuable alternative to antibody technology.

In Chemistry and Materials Sciences, the facile isolation of specific binding molecules may be useful for purposes as diverse as the generation of biosensors, the acceleration of chemical reactions, the design of materials with novel properties, the selective capture/separation/immobilization of target molecules.

The generation of large repertoires of molecules (e.g., by combinatorial chemistry; Otto S, Furlan R L, Sanders J K. Dynamic combinatorial chemistry. Drug Discov Today. (2002) 7: 117-125), coupled to ingenious screening methodologies, is recognized as an important avenue for the isolation of desired binding specificities. For example, most large pharmaceutical companies have proprietary chemical libraries, which they search for the identification of lead compounds. These libraries may be as large as >1 million members and yet, in some instances, not yield the binding specificities of interest [Balm H J, Stahl M. Structure-based library design: molecular modeling merges with combinatorial chemistry. Current Opinion in Chemical Biology (2000) 4: 283-286]. The screening of libraries containing millions of compounds may require not only very sophisticated synthetic methods, but also complex robotics and infrastructure for the storage, screening and evaluation of the members of the library.

The generation of large macromolecular repertoires (e.g., peptide or protein libraries), together with efficient biological and/or biochemical methods for the identification of binding specificities (such as phage display [Winter, 1994], peptides on plasmids [Cull M G, Miller J F, Schatz P J. Screening for receptor ligands using large libraries of peptides linked to the C terminus of the lac repressor. Proc Natl Acad Sci USA. (1992) 89: 1865-1869] ribosome display [Schaffitzel C, Hanes J, Jermutus L, Pluckthun A. Ribosome display: an in vitro method for selection and evolution of antibodies from libraries. J Immunol Methods. (1999) 231: 119-135] yeast display [Boder E T, Wittrup K D. Yeast surface display for screening combinatorial polypeptide libraries. Nat. Biotechnol. (1997) 15: 553-557], periplasmic expression with cytometric screening [Chen G, Hayhurst A, Thomas J G, Harvey B R, Iverson B L, Georgiou G. Isolation of high-affinity ligand-binding proteins by periplasmic expression with cytometric screening (PECS). Nat Biotechnol. (2001) 19:537-542], iterative colony filter screening [Giovannoni L, Viti F, Zardi L, Neri D. Isolation of anti-angiogenesis antibodies from a large combinatorial repertoire by colony filter screening. Nucleic Acids Res. (2001) 29: E27] etc.) may allow the isolation of valuable polypeptide binders, such as specific monoclonal antibodies, improved hormones and novel DNA-binding proteins. In contrast to conventional chemical libraries, protein libraries in the embodiments mentioned above may allow the efficient screening of as many as 1-10 billion individual members, in the search of a binding specificity of interest. On one hand, the generation of libraries of genes (e.g., the combinatorial mutagenesis of antibody genes; Winter, 1994; Viti F, Nilsson F, Demartis S, Huber A, Neri D. Design and use of phage display libraries for the selection of antibodies and enzymes. Methods Enzymol. (2000) 326:480-505) can directly be translated into libraries of proteins, using suitable expression systems (e.g. bacteria, yeasts, mammalian cells). Furthermore, methods such as phage display produce particles in which a phenotype (typically the binding properties of a protein, displayed on the surface of filamentous phage) is physically coupled to the corresponding genotype (i.e., the gene coding for the protein displayed on phage) [Winter, 1994], allowing the facile amplification and identification of library binding members with the desired binding specificity.

However, while biological/biochemical methods for the isolation of specific binding biomacromolecules can provide very useful binding specificities, their scope is essentially limited to repertoires of polypeptides or of nucleic acids [Brody E N, Gold L. Aptamers as therapeutic and diagnostic agents. J Biotechnol. (2000) 74:5-13]. For some applications, large biomacromolecules (such as proteins or DNA) are not ideal. For example, they are often unable to efficiently cross the cell membrane, and may undergo hydrolytic degradation in vivo.

In an attempt to mimic biological/biochemical methods for the identification of organic molecules with desired binding properties, out of a chemical library, Brenner and Lerner [Brenner S, Lerner R A. Encoded combinatorial chemistry. Proc Natl Acad Sci USA. (1992) 89: 5381-5383] have proposed the use of encoded chemical libraries (ECL). In their invention, the authors conceived a process of alternating parallel combinatorial synthesis in order to encode individual members of a large library of chemicals with unique nucleotide sequences. In particular, the authors postulated the combinatorial synthesis of polymeric chemical compounds on a solid support (e.g., a bead), where a step in the combinatorial synthesis would be followed by the synthesis (on the same bead) of a DNA sequence, to be used as a "memory tag" for the chemical reactions performed on the bead. In typical applications, DNA-encoded beads would be incubated with a target molecule (e.g., a protein of pharmaceutical relevance). After the DNA-tagged bead bearing the polymeric chemical entity is bound to the target, it should be possible to amplify the genetic tag by replication and use it for enrichment of the bound molecules by serial hybridization to a subset of the library. The nature of the polymeric chemical structure bound to the receptor could be decoded by sequencing the nucleotide tag.

The ECL method has the advantage of introducing the concept of "coding" a particular polymeric chemical moiety, synthesized on a bead, with a corresponding oligonucleotidic sequence, which can be "read" and amplified by PCR. However, the ECL method has a number of drawbacks. First, a general chemistry is needed which allows the alternating synthesis of polymeric organic molecules (often with different reactivity properties) and DNA synthesis on a bead. Second, the synthesis, management and quality control of large libraries (e.g., >1 million individual members) remains a formidable task. In fact, the usefulness of the ECL method has yet to be demonstrated with experimental examples.

PRIOR ART

From U.S. Pat. No. 5,573,905 an encoded combinatorial chemical library is known which comprises a plurality of bifunctional molecules according to the formula A-B-C, where A is a polymeric chemical moiety. B is a linker molecule operatively linking A and C, consisting of a chain length of 1 to about 20 atoms and preferably comprising means for attachment to a solid support. C is an identifier oligonucleotide comprising a sequence of nucleotides that identifies the structure of the chemical moiety. The attachment to a solid support is especially preferred when synthesizing step by step the chemical moiety (a polymer built of subunits $X_{1-n}$) and the oligonucleotide (built of nucleotides $Z_{1-n}$ which code for and identify the structure of the chemical subunits of the polymer). Also described are the bifunctional molecules of the library, and methods of using the library to identify chemical structures within the library that bind to biological active molecules in preselected binding interactions. Utilizing the code C for the identification of the polymer A and attaching the code C to the polymer A with a linker molecule B allows the polymer to be identified exactly, however, the solution presented in U.S. Pat. No. 5,573,905 (which basically is the same as published by Brenner and Lerner, 1992) is limited to this special type of a chemical moiety. The fact that individual synthesis has to be carried out for each individual of a chemical library is regarded as another disadvantage.

OBJECTS OF THE INVENTION

It is therefore an object of the present invention to provide a chemical compound comprising a chemical moiety of any kind capable of performing a binding interaction with a target molecule (e.g. a biological target) and further comprising an oligonucleotide or functional analogue thereof which chemical compound does not need to be individually synthesized in order to build up a chemical library.

This object is met according to a first aspect by the combination of features of independent claim 1, defining a chemical compound comprising a chemical moiety (p) capable of performing a binding interaction with a target molecule (e.g. a biological target) and further comprising an oligonucleotide (b) or functional analogue thereof which is characterized in that the oligonucleotide (b) or functional analogue comprises at least one self-assembly sequence (b1) capable of performing a combination reaction with at least one self-assembly sequence (b1') of a complementary oligonucleotide or functional analogue bound to another chemical compound comprising a chemical moiety (q).

This object is met according to a second aspect by the combination of features of independent claim 3, defining a chemical compound comprising a chemical moiety (p) capable of performing a binding interaction with a target molecule (e.g. a biological target) and further comprising an oligonucleotide (b) or functional analogue thereof, which comprises a coding sequence (b1) coding for the identification of the chemical moiety (p), and which is characterized in that the chemical compound further comprises at least one self-assembly moiety (m) capable of performing a combination reaction with at least one self-assembly moiety (m') of a another chemical compound comprising a chemical moiety (q).

Further aspects and features of the present invention derive from the dependent claims.

SUMMARY OF THE INVENTION

In our invention, we reasoned that a key contribution to the generation (and screening) of very large chemical libraries may come from the "self-assembly" of encoded molecules. In particular, we reasoned that self-assembly (e.g., by homodimerization, heterodimerization or multimerization) of DNA-tagged chemical entities would represent an avenue for the facile generation of very large DNA-tagged chemical libraries, starting from smaller DNA-tagged chemical libraries. For example, self-assembly (heterodimerization) of two libraries containing 1000 members would yield 1,000,000 different combinations, i.e. 1,000,000 different chemical entities. Notably, homo- or hetero-trimerization of encoded libraries containing 1000 DNA-tagged members would yield a library containing 1,000,000,000 different DNA-tagged combinations, i.e. chemical entities. Thus, the present invention provides a chemical compound comprising a chemical moiety of any kind capable of performing a binding interaction with a target molecule (e.g. a biological target) and further comprising an oligonucleotide or functional analogue thereof which can be synthesized separately and then coupled together. The resulting chemical derivative(s) of the oligonucleotide can further assemble with other similar compounds to generate higher order structures and encoded libraries of compounds.

For illustrative purposes, one particular embodiment of our invention is depicted in FIG. 1. Two chemical libraries are synthesized by chemical modification of the 3' end and the 5' end, respectively, of oligonucleotides capable of duplex formation and which carry distinctive "sequence tags" (associated with [and therefore "coding for"] the chemical moiety attached to their extremity). The resulting encoded self-assembled chemical library (ESACHEL) can be very large (as it originates from the combinatorial self-assembly of two smaller libraries) and can be screened for binding to a biological target (e.g., a protein of pharmaceutical interest). Those members of the library which display suitable binding specificities can be captured with the target of interest (for example, using a target immobilized on a solid support). Their genetic code, encoding the chemical entity responsible for the binding specificity of interest, can then be retrieved using a number of ingenious methods, which are described in the section "Description of the Invention" (see below).

DEFINITIONS

Specific Binding Members:

This describes a member of an ensemble of 2, 3 or more molecules, which have binding specificity for one another. A specific binding member may be naturally derived or wholly or partially synthetically produced. One member of an ensemble of specifically binding molecules has an area on its surface, or a cavity, which specifically binds to and is therefore complementary to a particular spatial and polar organization of one or more members of the ensemble of molecules. Thus the members of specific binding pairs have the property of binding specifically to each other.

Specific:

This may be used to refer to the situation in which one member of a specific binding pair will not show any significant binding to molecules other than its specific binding partner(s). In general, specificity is associated with a significant difference in binding affinity, relative to "non-specific" targets. The term is also applicable where e.g. a binding member is specific for a particular surface on the target molecule (hereafter termed as "epitope"), in which case the specific binding member with this specificity will be able to bind to various target molecules carrying the epitope.

FIGURE CAPTIONS

FIG. 1: a Simple Embodiment of ESACHEL Technology:

In a simple embodiment of ESACHEL technology, two chemical libraries are synthesized by individual chemical modification of the 3' end and the 5' end, respectively, of oligonucleotides capable of partial heteroduplex formation and which carry distinctive "sequence tags" (associated with [and therefore "coding for"] the chemical moieties p and q attached to their extremity). The resulting encoded self-assembled chemical library (ESACHEL) can be very large (as it originates from the combinatorial self-assembly of two smaller libraries) and can be screened for binding to a biological target (e.g., a protein of pharmaceutical interest). Those members of the library which display suitable binding specificities can be captured with the target of interest (for example, using a target immobilized on a solid support). Their genetic code, encoding the chemical entity responsible for the binding specificity of interest, can then be retrieved using a number of ingenious methods FIG. 2: Generalization of the ESACHEL Design:

The main ingredients of ESACHEL technology are chemical compounds, comprising an oligonucleotidic moiety (typically, a DNA sequence) linked to an oligomerization domain [capable of mediating the (homo- or hetero-) dimerization, trimerization or tetramerization of the chemical compounds], linked to a chemical entity, which may be involved in a specific binding interaction with a target molecule. Part of the sequence of the oligonucleotidic moiety will be uniquely associated with the chemical entity (therefore acting as a "code"). The oligomerization domain and the code can be distinct portions of the same molecule (typically an oligonucleotide).

Figure 3:
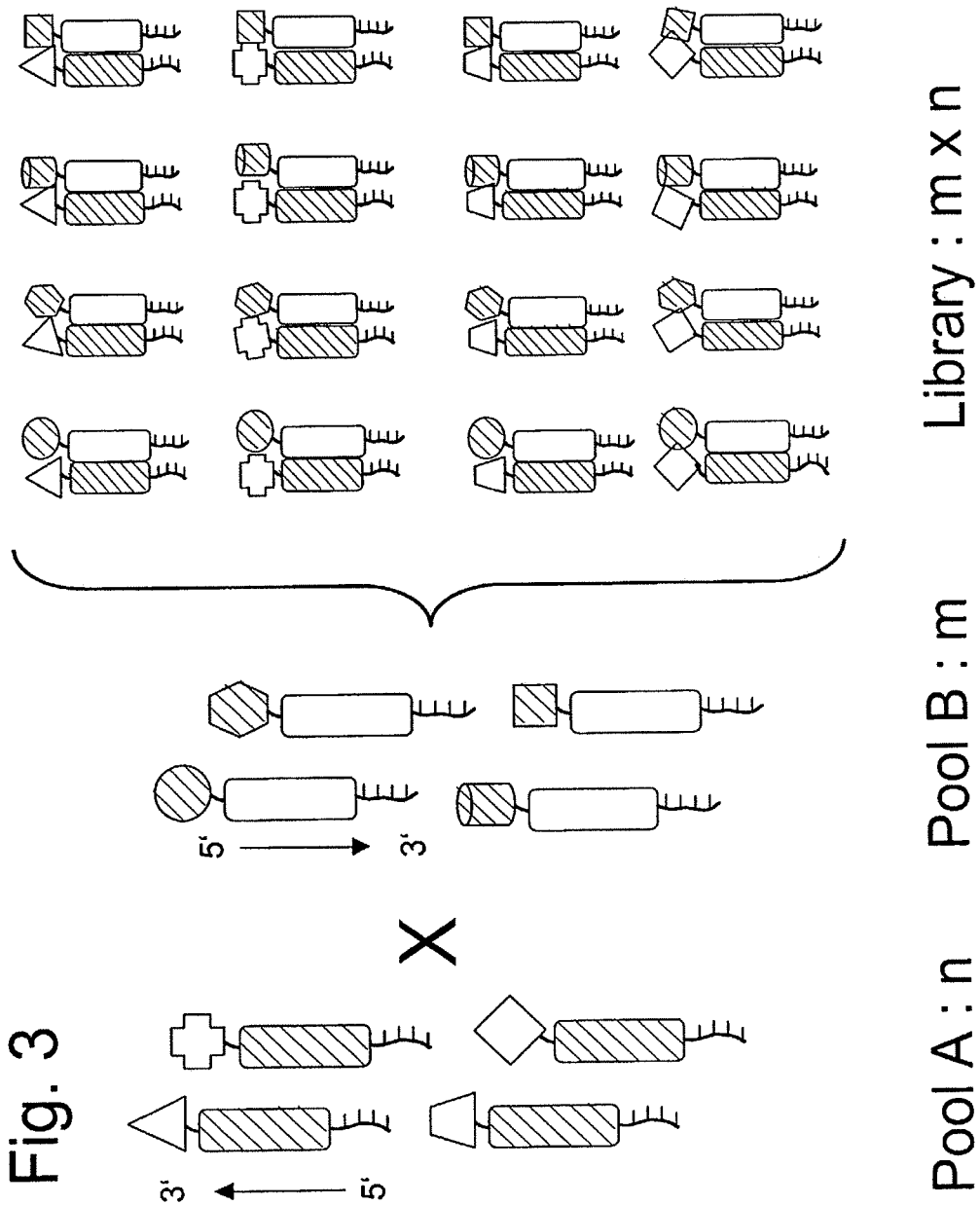

FIG. 3: Self-Assembly of Individual ESACHEL Chemical Compounds can Yield Combinatorial Libraries of Large Size:

In a practical embodiment of ESACHEL technology, a number n of different chemical compounds, carrying a thiol-reactive moiety (e.g., a maleimido or a iodoacetamido group), are reacted (in separate reactions) with n different DNA oligonucleotides, carrying a thiol group at the 3' end. The corresponding pool of n conjugates is indicated in the Figure as "pool A". Similarly, a number m of different chemical compounds, carrying a thiol-reactive moiety (e.g., a maleimido or a iodoacetamido group), are reacted (in separate reactions) with m different DNA oligonucleotides, carrying a thiol group at the 5' end. The corresponding pool of m conjugates is indicated in the Figure as "pool B". The resulting self-assembled library members will correspond to m×n combinations. A number of other methodologies may be used in order to chemically couple molecules to oligonucleotides (e.g., use oligonucleotides carrying a primary amino group at their extremity, for the coupling to activated esters).

Figure 4:
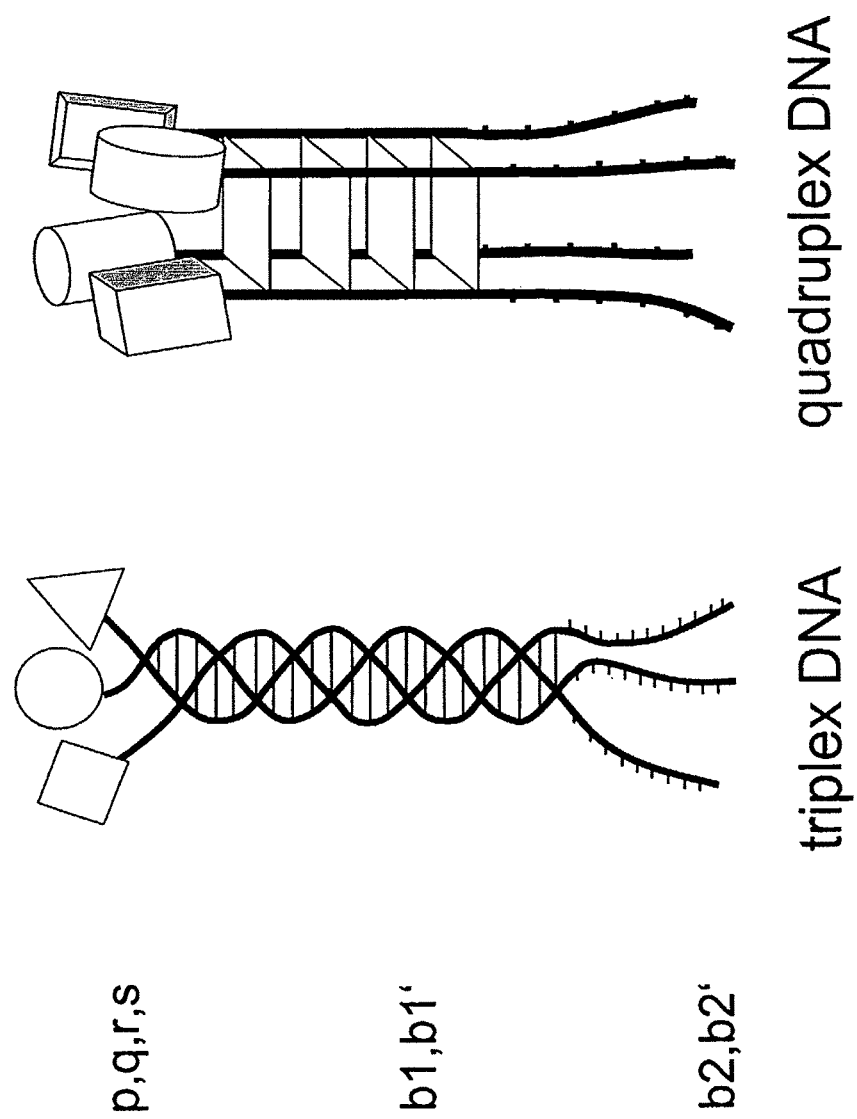

FIG. 4: Large Library Sizes can be Achieved by ESACHEL Embodiments, in Which Trimerization Domains or Tetramerization Domains are DNA Sequences Forming Triplexes or Quadruplexes:

Certain DNA sequences are known to be capable of forming stable trimeric complexes or stable tetrameric complexes. For example, Hoogsten pairing of DNA triplexes could allow the self-assembly of Pools A×B×C, containing n, m and l members, respectively. The tetrameric assembly of DNA-(chemical moiety) conjugates would allow even larger library sizes, starting from sub-libraries A, B, C and D of small dimension.

Figure 5:
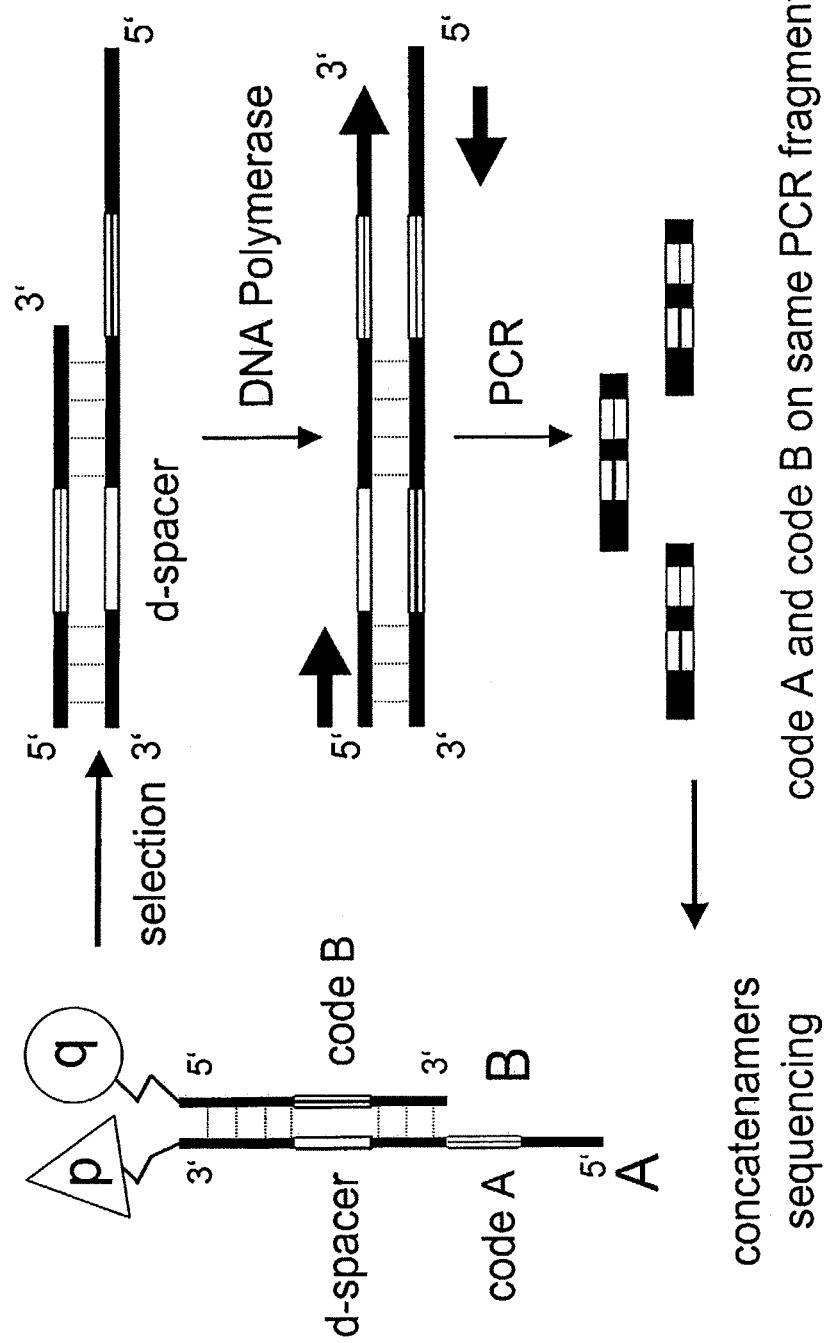

FIG. 5: One Method of ESACHEL Decoding:

The oligonucleotides of sub-library A bear chemical entities at the 3' end. Towards the 3' extremity, the DNA sequence is designed to hybridize to the DNA sequences at the 5' extremity of oligonucleotides of sub-library B. The hybridization region is interrupted by a small segment. In sub-library A, this small segment is conveniently Composed of phosphodiester backbone without bases (termed d-spacer in the Figure); in sub-library B, the corresponding short segment will have unique sequence for each member of the sub-library (therefore acting as "code" for the sub-library B). By contrast, oligonucleotides of sub-library A have their distinctive code towards the 5' extremity.

After biopanning, oligonucleotides of sub-library B remain stably annealed to oligonucleotides of sub-library A, and can work as primers for a DNA polymerase reaction on the template A. The resulting DNA segment, carrying both code A and code B, can be amplified (typically by PCR), using primers which hybridize at the constant extremities of the DNA segment.

Figure 6:
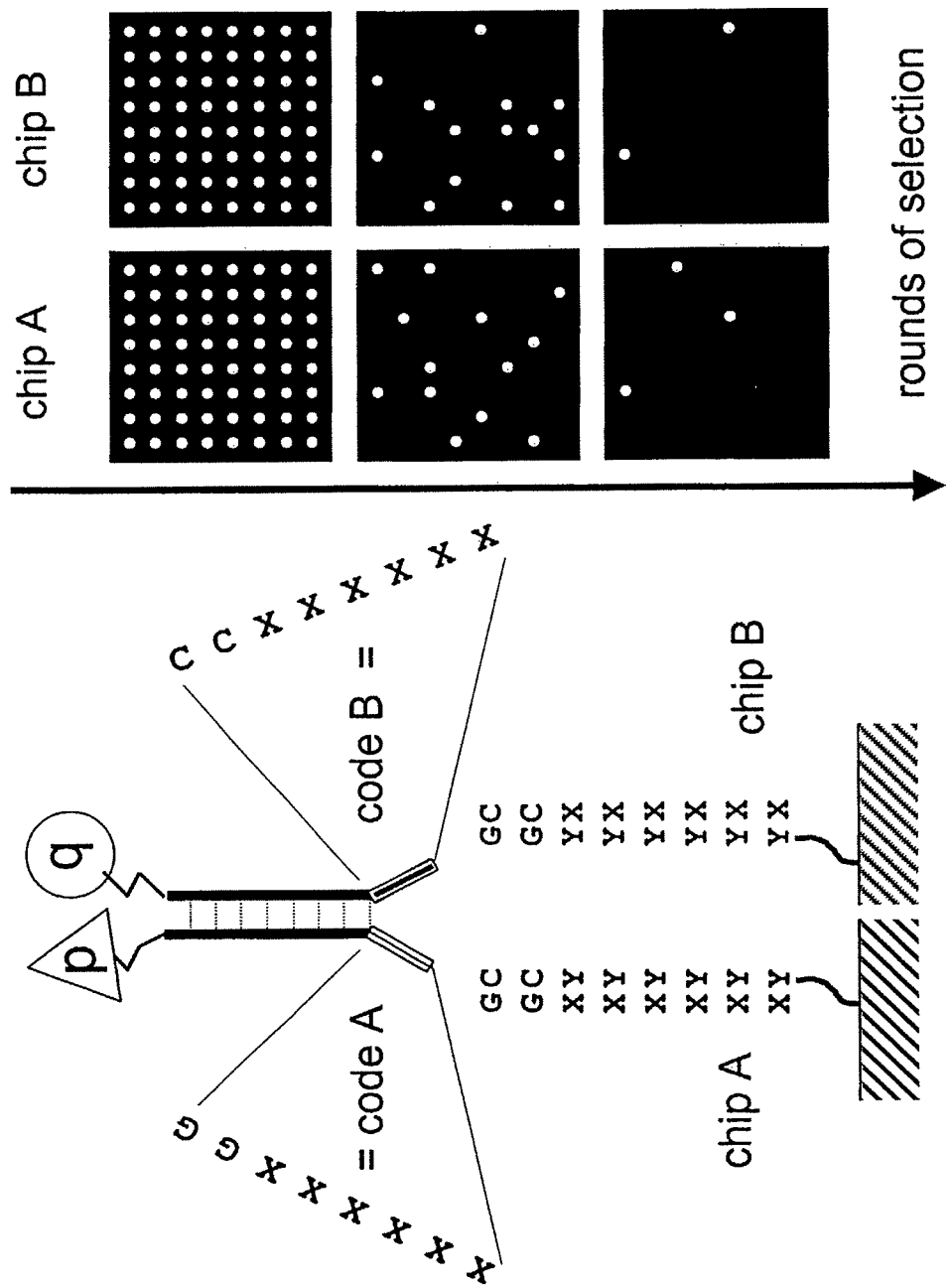

FIG. 6: a General Method of ESACHEL Decoding:

The identity of specific binders, isolated from sub-libraries A and B carrying chemical moieties at the extremities of partially-annealing oligonucleotides, is established by hybridization with target oligonucleotides immobilized on one or more chips. Such chips preferably are made from silicon wafers with attached oligonucleotide fragments. For example, chip A will allow the reading of the identity (and frequency) of members of sub-library A, rescued after a biopanning experiment. Similarly, chip B will allow the reading of the identity (and frequency) of members of sub-library B. In a first step, the decoding method depicted in the Figure will not provide information about the pairing of code A and code B within specific binding members. However, decoding on chip A and B will suggest candidate components of sub-libraries A and B, to be re-annealed and screened in a successive round of bio-panning. Increasingly stringent binding to the target will be mirrored by a reduction in the number of A and B members, identified on the chip. Ultimately, the possible combinations of the candidate A and B members will be assembled individually (or in smaller pools), and assayed for binding to the target.

Figure 7:
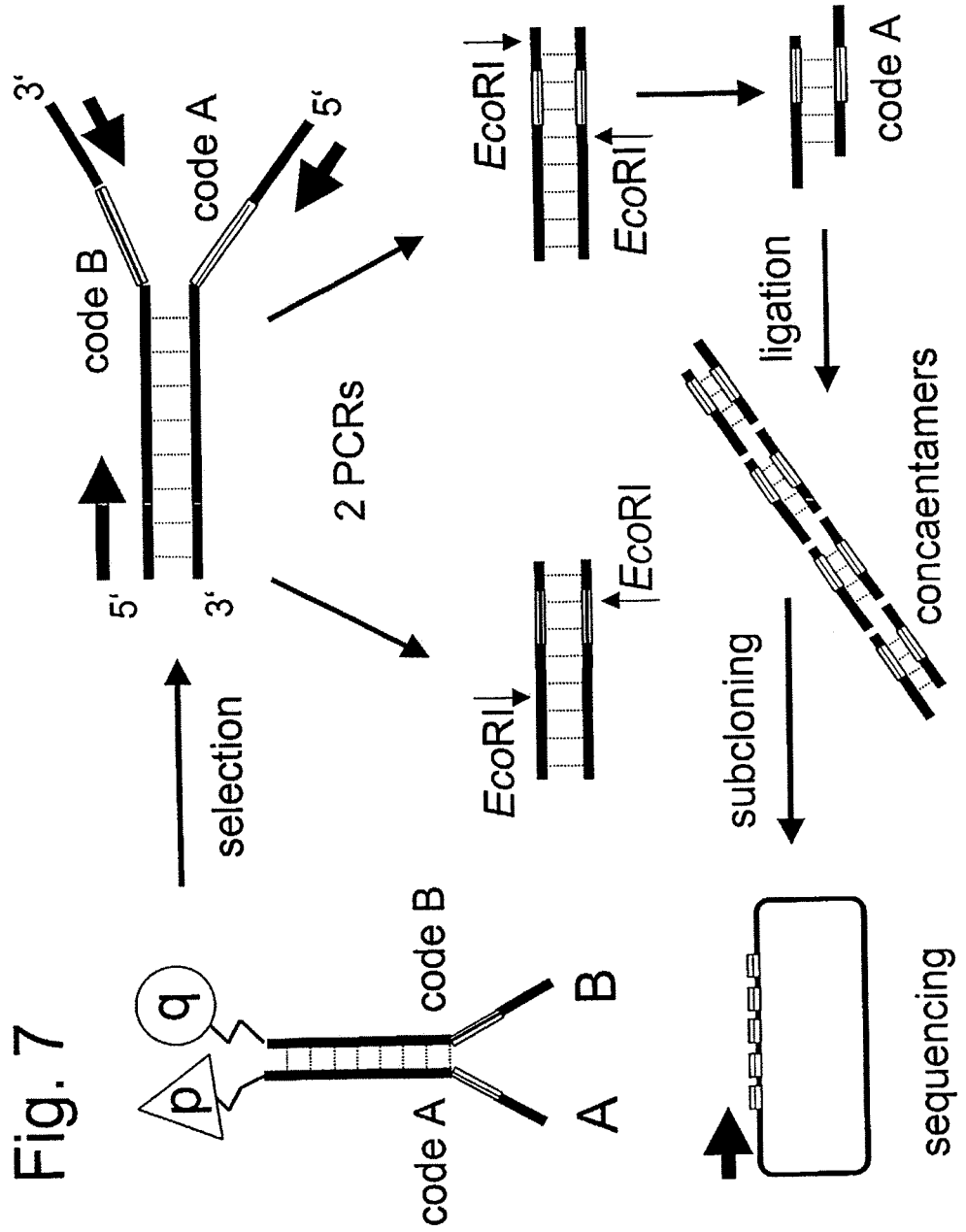

FIG. 7: a PCR-Based Method for ESACHEL Deconvolution:

Sub-libraries A and B form a heteroduplex, flanked by unique sequences coding for the different library members and by constant DNA segments at the termini. After biopanning, suitable pairs of primers allow the PCR amplification of the two strands, yielding PCR products whose sequence can be identified using standard methods (e.g. by concatenation of the PCR products, followed by subcloning and sequencing. A deconvolution procedure may be applied (consisting of one or more rounds of panning, followed by sequencing and by the choice of a restricted set of sub-library components for the next ESACHEL screening), restricting the number of candidate ESACHEL members capable of giving specific binders after self-assembly.

Figure 8:
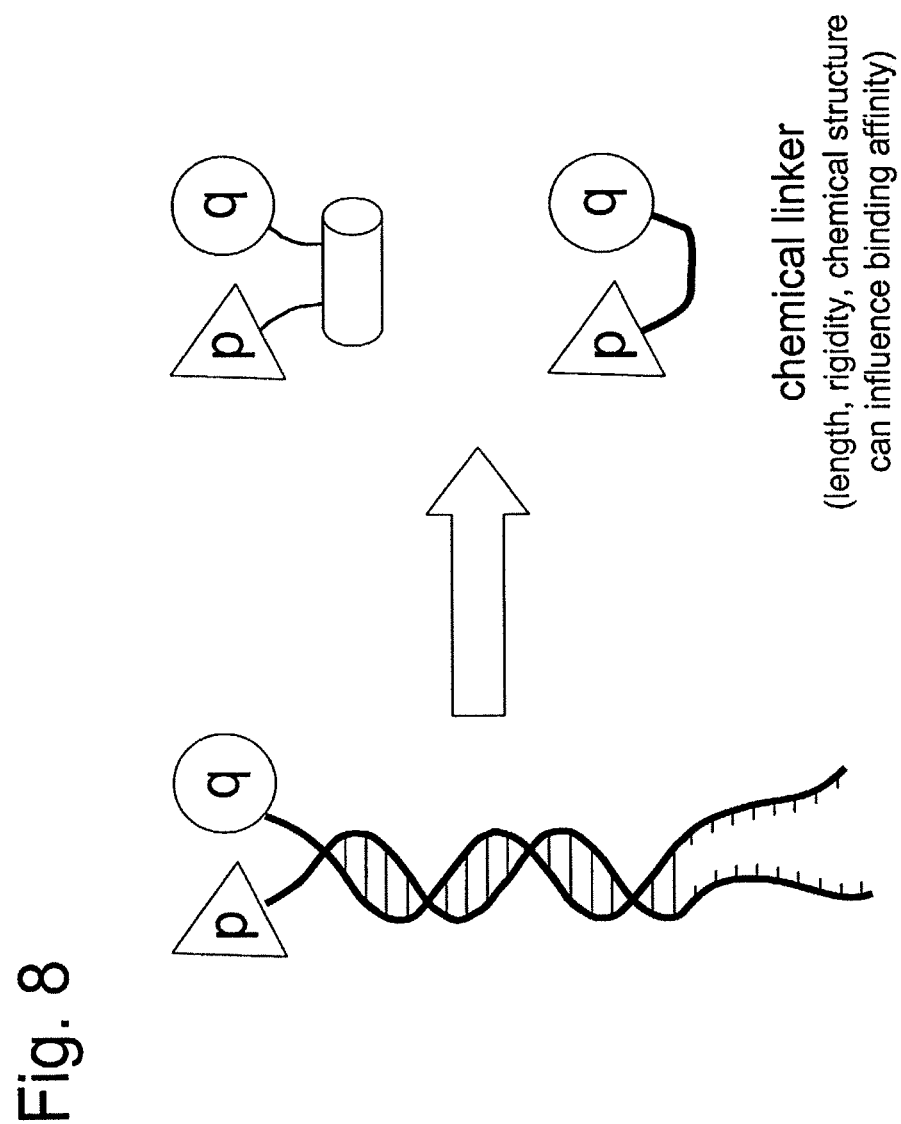

FIG. 8: Converting ESACHEL Ligands into Covalently-Linked Chemical Moieties:

In many ESACHEL embodiments, chemical derivatives of self-assembling oligonucleotides will be isolated at the end of one or more rounds of panning. For many applications, it will be desirable to covalently link together the chemical moieties, responsible for the interaction with the target molecule of interest. The length, rigidity, stereoelectronic chemical properties and solubility of the linker will influence the binding affinity and performance of the resulting molecule.

Figure 9:
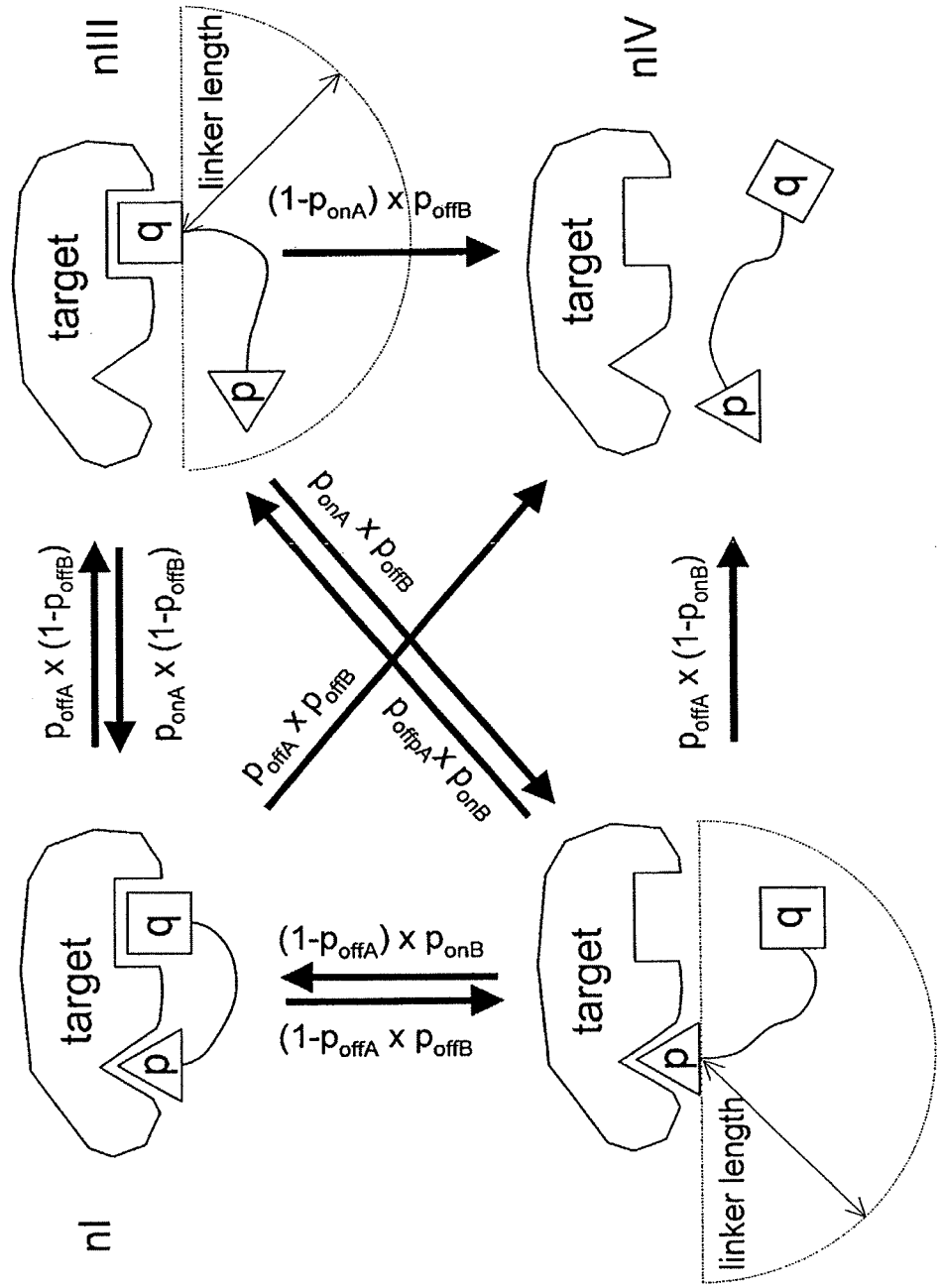

FIG. 9: Chemical Equilibria Contributing to the Chelate Effect:

The diagram shows the possible states of the interactions between a bidentate ligand (A-B) binding to a target molecule. In state nI, both A and B moieties are bound to their respective binding pockets. In state nII and nIII only moiety A or B are bound, respectively. In state nIV, the compound A-B is dissociated from the target.

Figure 10:
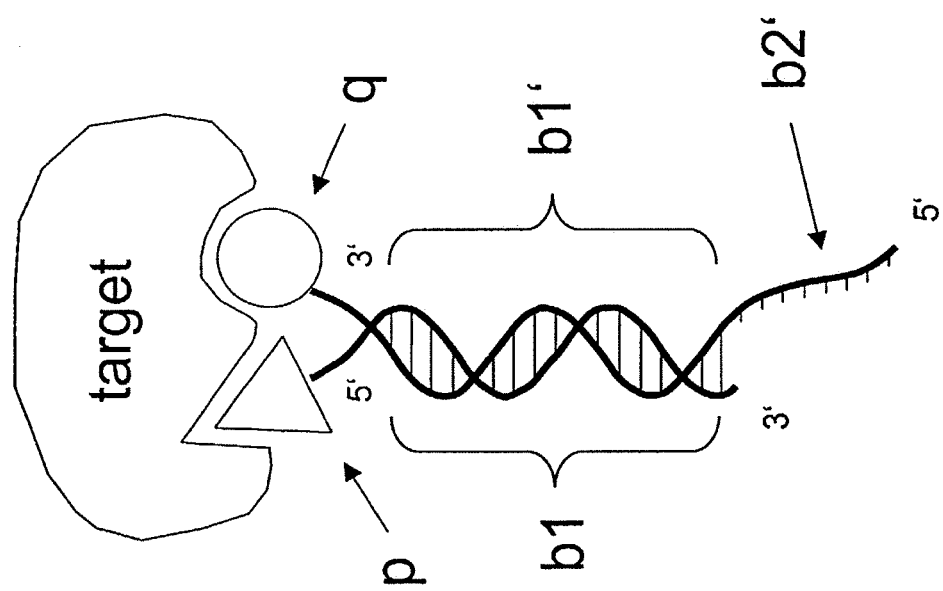

FIG. 10: Assembly of molecule p with molecular repertoire Q: The diagram shows heteroduplex formation between an oligonucleotide, coupled to a low-affinity binder p, and a second class of oligonucleotides, which bear chemical moieties q and distinctive codes, capable of identifying the molecules q which synergise with p for binding to a target molecule (e.g., a protein target).

Figure 11:
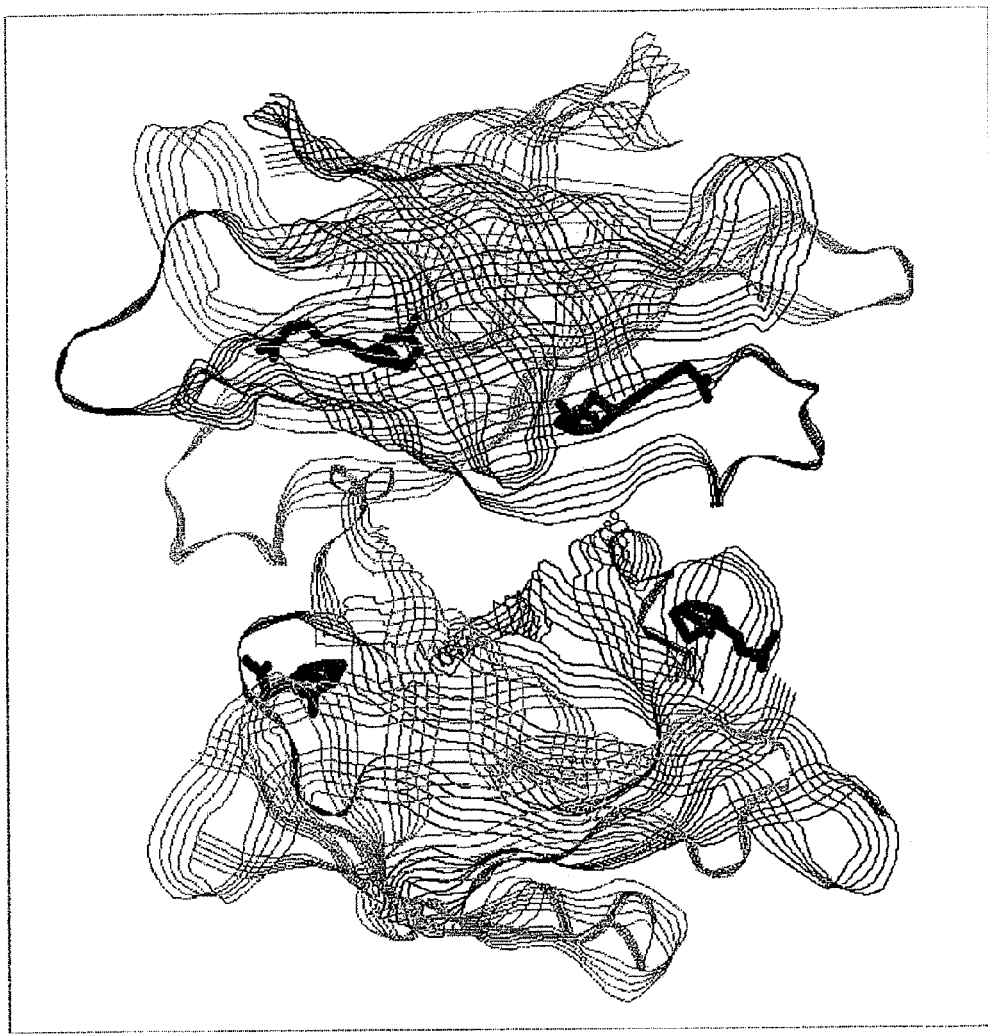

FIG. 11: Biotin molecules binding to a streptavidin homotetramer: Four biotin molecules binding to their respective binding sites on a streptavidin homotertramer. (1SWG.pdb: Chu et al. (1998), Thermodynamic and structural consequences of flexible loop deletion by circular permutation in the streptavidinbiotin system. Protein Sci 7 pp. 848) are shown.

Figure 12:
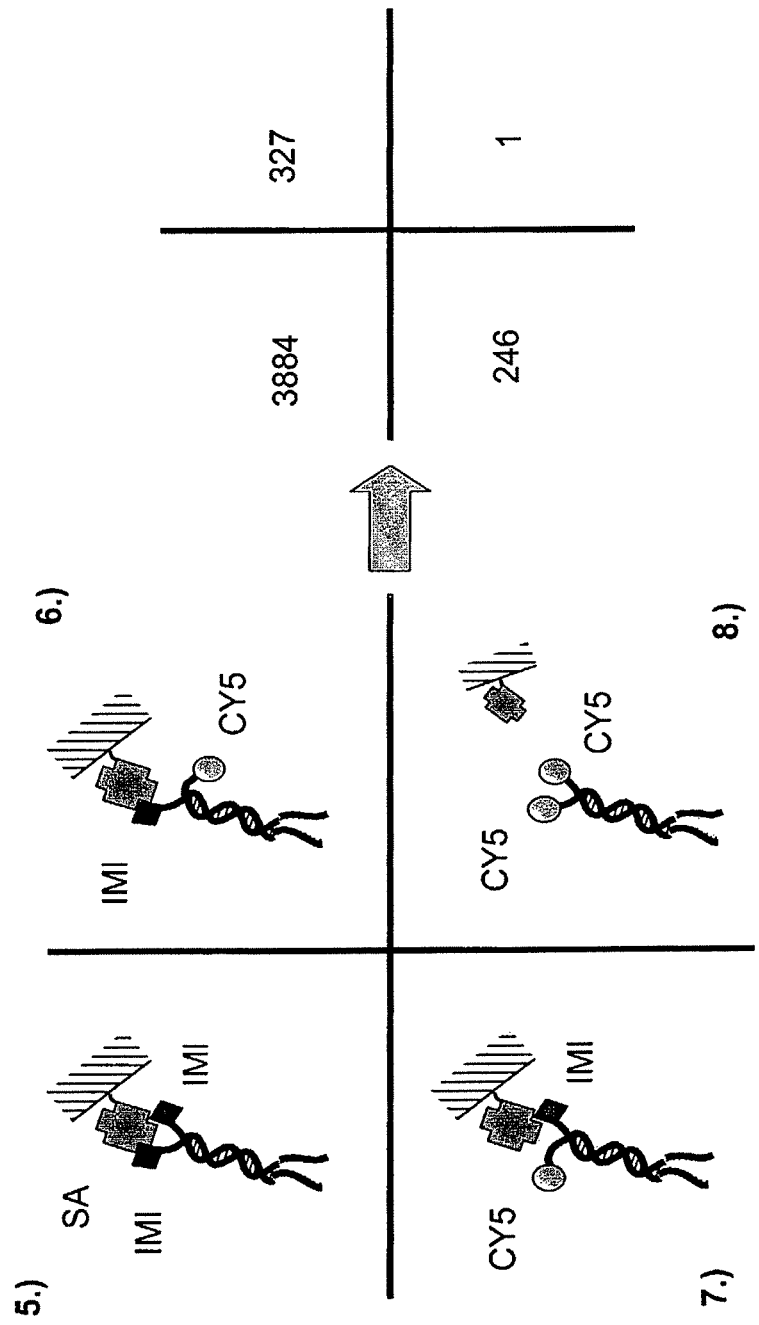

FIG. 12: the Results from Experiment 6:

The results show that, even in this non-optimized selection experiment, the bidendate ligand in ESACHEL format is preferentially enriched, compared to ESACHEL compounds carrying a single streptavidin ligand or no streptavidin ligand at all (IMI=iminibiotin, SA=Streptavidin).

Figure 13:
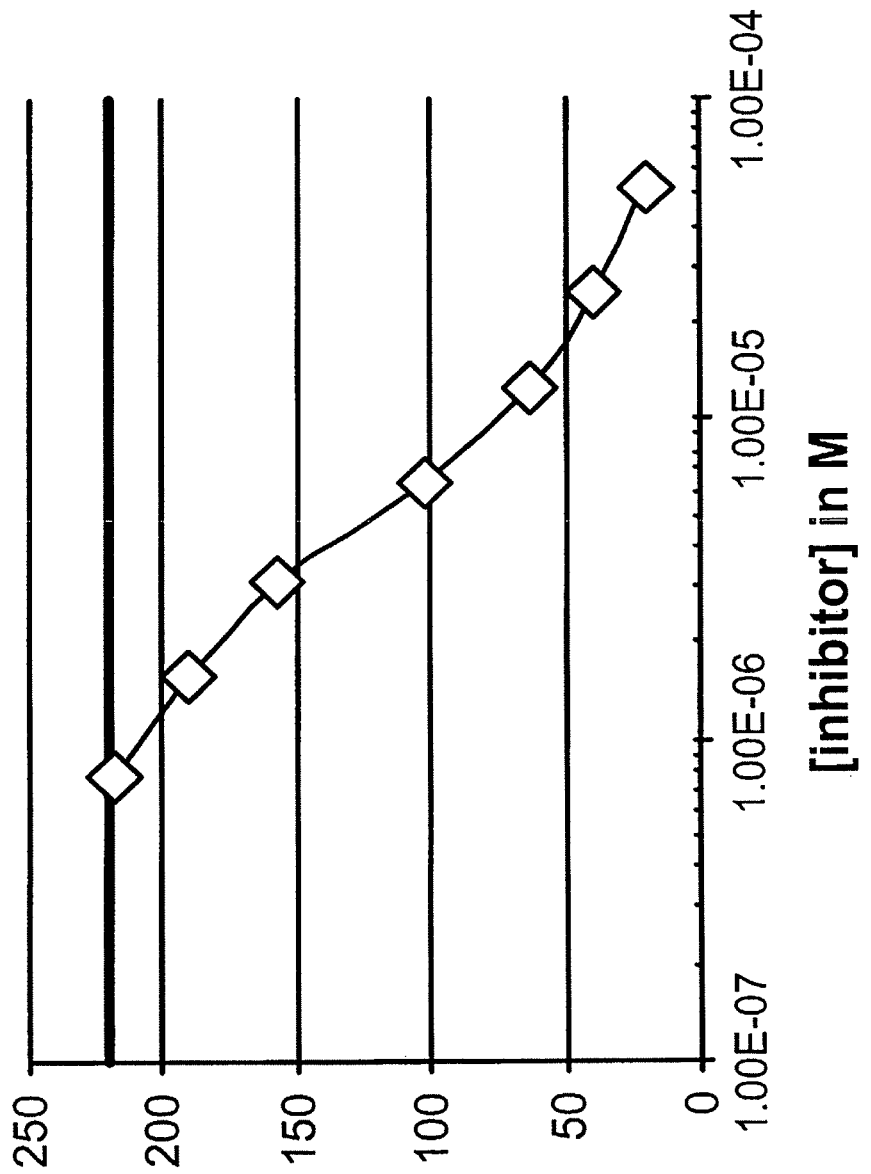

FIG. 13: the Results from Experiment 7:

The results of this experiment are plotted and show that 4-sulfonamido benzoic acid propylamide has an 1050 of 6 μM towards human carbonic anhydrase.

A computer program has been written for the approximate evaluation of the contribution of the chelate effect to the residence time of A-B on the target in irreversible dissociation conditions, as a function of kinetic association and dissociation constants of the moieties A and B towards their respective binding pockets, and of the linker length between A and B. The probability that one moiety dissociates per time unit is indicated as "poII". The probability that one moiety binds to the target per time unit is indicated as "pon".

DESCRIPTION OF THE INVENTION

Figure 2:
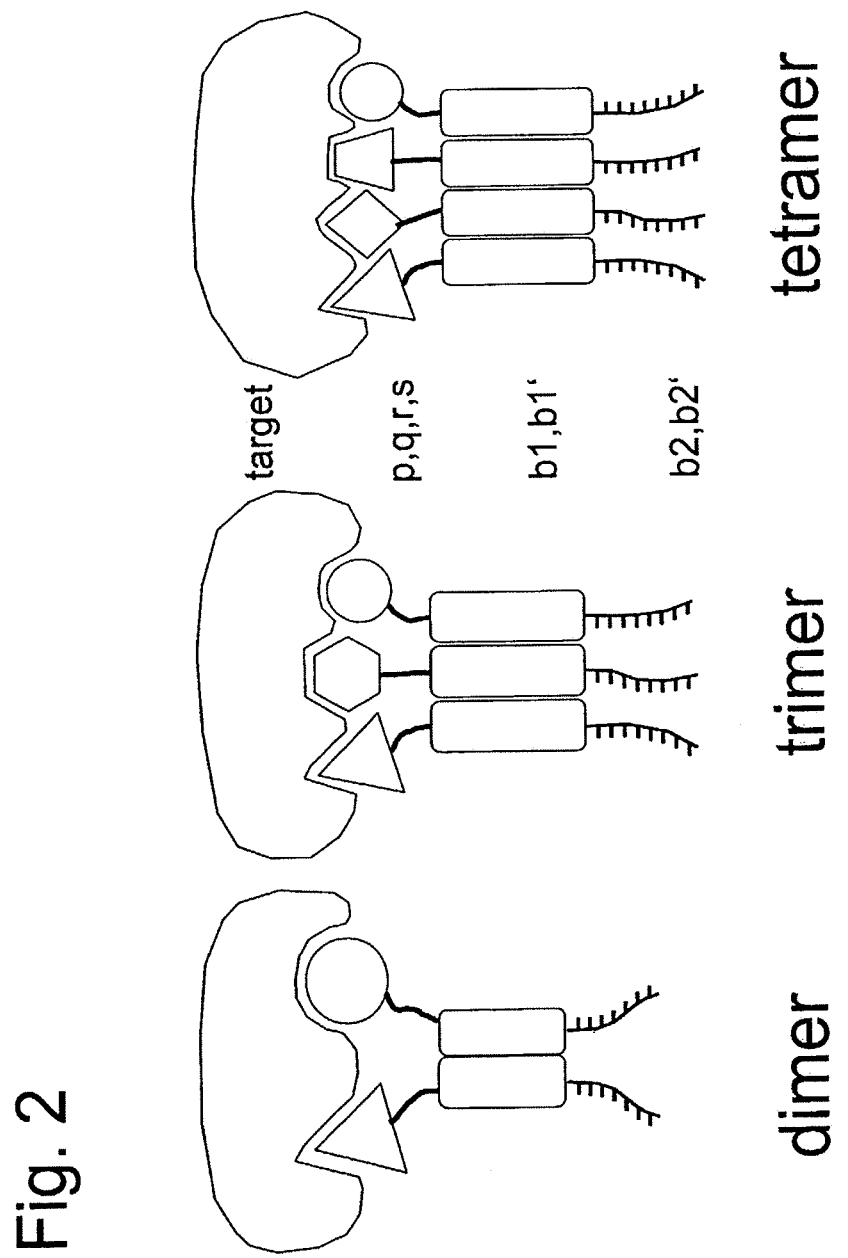

The main ingredients of ESACHEL technology are chemical compounds, comprising an oligonucleotidic moiety (typically, a DNA sequence) linked to an oligomerization domain [capable of mediating the (homo- or hetero-) dimerization, trimerization or tetramerization of the chemical compounds], linked to a chemical entity, which may be involved in a specific binding interaction with a target molecule (FIG. 2). Part of the sequence of the oligonucleotidic moiety will be uniquely associated with the chemical entity (therefore acting as a "code"). In many cases, portions of the same oligonucleotide will serve as the oligomerization domain and the code.

Oligonucleotidic Moiety:

The nature and the design of the oligonucleotidic moieties in ESACHEL technology is best understood by the description of the "coding" system, provided in the sections below and in the Examples. As an introduction, it suffices to say that, by stably associating chemical entities with a unique oligonucleotidic sequence (e.g., a sequence of DNA or DNA analogues), one provides that chemical entity with a unique code, which can be "read" in a variety of ways (sequencing, hybridization to DNA chips, etc.) and which may be amenable to amplification (e.g., by the use of the polymerase chain reaction [PCR]). Furthermore, using ingenious methods described below, the code of one particular chemical compound may become physically linked to the code of other chemical compound(s), when these chemical compounds are associated by means of an oligomerization domain.

Oligomerization Domains:

Suitable DNA sequences (capable of heteroduplex, triplex [Strobel S A, Dervan P B. Single-site enzymatic cleavage of yeast genomic DNA mediated by triple helix formation.

Nature. (1991) 350:172-174] or quadruplex [Various authors. Issue of *Biopolymers* (2000-2001), volume 56 (3)] formation), can be considered as possible oligomerization domains.

Alternatively, the use of other self-assembling polypeptides (e.g. amphipathic peptide helices such as leucine zippers) could be considered. Many more chemical moieties could be considered as mediators of chemically defined, oligomeric moieties. For instance, complexes of metal atoms with suitable ligands [such as dipyridyl or tripyridyl derivatives) could be envisaged. Furthermore, one could envisage that a non-covalent interaction would bring together different chemical compounds, which could then react with one another and become covalently associated.

Some Practical Embodiments of ESACHEL Technology:

In order to illustrate one possible practical embodiment of ESACHEL technology, let us consider the following example (depicted in FIG. 3).

A number n of different chemical compounds, carrying a reactive moiety (e.g. a thiol-reactive maleimido or a iodoacetamido group), are reacted (in separate reactions) with n different DNA oligonucleotides, carrying a reactive moiety (e.g. a thiol group at the 3' end). The corresponding pool of n conjugates is indicated in the Figure as "pool A". The oligonucleotides of pool A are designed to have:

one portion of the DNA sequence which can hybridize to compounds of pool B (see FIG. 3 and comments below)

a distinctive DNA sequence for each of the n members of Pool A additional portions of the DNA sequence judiciously designed for "decoding" binding combinations (optional; see below in the section about "Decoding" and in the Examples).

Similarly, a number m of different chemical compounds, carrying a thiol-reactive moiety (e.g., a maleimido or a iodoacetamido group), are reacted (in separate reactions) with m different DNA oligonucleotides, carrying a thiol group at the 5' end. The corresponding pool of m conjugates is indicated in the Figure as "pool B". Applications could be conceived in which the numbers of compounds and oligonucleotides are different [e.g., more compounds "encoded" by the same oligonucleotide].

The oligonucleotides of pool B are designed to have:

one portion of the DNA sequence which can hybridize to compounds of pool A (see FIG. 3)

a distinctive DNA sequence for each of the m members of Pool B additional portions of the DNA sequence judiciously designed for "decoding" binding combinations (optional).

The partially complementary strands of the DNA conjugates of pool A and pool B can easily heterodimerize in solution, with comparable efficiency within the different n members of Pool A and the m members of Pool B. If suitable stoichiometric ratios of the compounds of Pool A and Pool B are used, the n different types of compounds of Pool A will heterodimerize with the m different types of compounds of Pool B, yielding a combinatorial self-assembled chemical library of dimension m×n. For example, two libraries of thousands of compounds would yield millions of different combinations. Furthermore, the resulting self-assembled m×n combinations will carry unique DNA codes, corresponding to the non-covalent but stable association (heterodimerization) of the DNA code of the member of Pool A with the DNA code of the member of Pool B.

As an alternative to the coupling of chemical entities to thiol-bearing oligonucleotides, a number of standard chemical alternatives can be considered (e.g., oligonucleotides carrying a phosphodiester bond at one extremity, forming chemical structures such as $—O—P(O)_2—O—(CH_2)_n—NH—CO—R$, where R may correspond to a number of different chemical entities, and n may range between 1 and 10).

Let us assume that one particular member of the library is capable of specific binding to a target of interest (e.g., a protein immobilized on a bead). Let us also assume that both strands A and B contributed to the specific binding interaction (for a discussion of the chelate effect which may facilitate this specific binding, see below). It should be possible to preferentially enrich this particular combination of A and B over the m×n combinations (for example, by exposing the library to the target protein on the bead, followed by the physical removal of the bead from the library solution, followed by judicious washing of the bead, to reduce the amount of non-specific binders on the bead). The analogy of this procedure to the biopanning procedures used with antibody phage libraries (Viti, 2000) should be evident to any person skilled in the art.

The rescue of the particular combination of A and B, displaying the desired binding specificity, can then be followed by the identification of the chemical entities responsible for the binding, by identifying the DNA codes of the two strands A and B [see later section on "decoding" for a discussion on possible strategies for the identification of the DNA codes].

For a number of applications, at the end of the ESACHEL procedure, it may be desirable to link the two chemical entities A and B, responsible for the specific binding to the target (FIG. 3). One may want to try a variety of different chemical linkers, and assess whether the resulting chemical compounds, derived from the chemical entities A and B, display desired molecular properties (e.g., high affinity for the target, high specificity for the target, suitable chemical stability, suitable solubility properties, suitable pharmacological properties, etc.). For example, the length of the chemical linker between A and B will dramatically influence the binding properties of the conjugate (for a discussion, see section below on the chelate effect).

In the case of FIG. 3, a DNA portion is used as heterodimerization domain, and thioether bond formation is used for the coupling of DNA oligonucleotides to chemical entities of the library. However, other oligomerization domains could be considered, as well as other chemical avenues for the coupling of chemical entities to DNA.

Certain DNA sequences are known to be capable of forming stable trimeric complexes [Strobel, 1991] or stable tetrameric complexes [Various authors, 2000-2001]. For example, Hoogsten pairing of DNA triplexes could allow the self-assembly of Pools A×B×C, containing n, m and l members, respectively (FIG. 4). The tetrameric assembly of DNA-(chemical moiety) conjugates would allow even larger library sizes, starting from sub-libraries A, B, C and D of small dimension. However, the decoding of binding interactions can, in some cases, be more difficult for trimeric and/or tetrameric self-assembled encoded libraries, as compared to dimeric libraries. Furthermore, the length and flexibility of the linkers between the DNA strands and the chemical moieties displayed at their extremity may either facilitate or hinder the identification of specific binding members of the encoded self-assembled chemical (ESACHEL) library. A certain degree of flexibility may allow suitable chemical moieties to find complementary pockets on the target molecule (FIG. 4). On the other hands, the affinity contribution of the chelate effect is expected to decrease with linker length.

It is worth mentioning that, starting from sub-libraries of 100 members, trimeric ESACHEL libraries would contain $10^6$ members, while tetrameric ESACHEL libraries would contain $10^8$ members. It is easy to calculate the resulting library size, starting from sub-libraries of different dimension. The large combinatorial complexity of encoded self-assembling chemical compounds may allow the identification of specific binding members, which have so far escaped identification using conventional combinatorial chemical methods. An analogy can be drawn from the field of antibody phage technology, where it was demonstrated that library size plays a crucial role in the isolation of high-affinity antibodies.
ESACHEL Codes and Decoding Methods:

In ESACHEL technology, unique oligonucleotidic sequences (typically, DNA sequences) provide chemical entities with a unique code. How many different sequences do we need, in order to identify members of a library?

As mentioned above, the key components of ESACHEL technology are chemical compounds, comprising an oligonucleotidic moiety (typically, a DNA sequence) linked to an oligomerization domain, in turn linked to a chemical entity. In most cases, the oligonucleotidic moiety will also provide the oligomerization domains. As a consequence, in most cases, ESACHEL components will be chemical entities coupled to judiciously chosen DNA oligonucleotides. Typically, such oligonucleotides will contain a constant part and a variable part (uniquely characteristic for each member of the library).

Let us consider, as an example, the case illustrated in FIG. 3, and discussed in the section "Some practical embodiments of ESACHEL technology" (see above). In this example, a sub-library "A" (containing n compounds attached at the 3' extremity of DNA oligonucleotides) is assembled to a sub-library "B" (containing m compounds attached at the 5' extremity of oligonucleotides). Sub-library A can be represented by a DNA sequence of x bases, where $4^x$ is greater or equal to n. Sub-library B can be represented by a DNA sequence of y bases, where $4^y$ is greater or equal to m. In most cases (see below), identification of the code of sub-library members also provides information about which sub-library a particular code (and therefore a particular compound) belongs to.

Many methods of "decoding" the ESACHEL codes could be envisaged. Below, we illustrate three, which correspond to different experimental requirements and which demonstrate the flexibility of ESACHEL technology.

Let us consider for simplicity the ESACHEL embodiment of FIG. 3. A convenient design of oligonucleotides, on which sub-libraries A and B are based, is depicted in FIG. 5. The oligonucleotides of sub-library A bear chemical entities at the 3' end. Towards the 3' extremity, the DNA sequence is designed to hybridize to the DNA sequences at the 5' extremity of oligonucleotides of sub-library B. The hybridization region is interrupted by a small segment. In sub-library A, this small segment is conveniently composed of phosphodiester backbone without bases (termed d-spacer in the Figure); in sub-library B, the corresponding short segment will have unique sequence for each member of the sub-library (therefore acting as "code" for the sub-library B). By contrast, oligonucleotides of sub-library A have their distinctive code towards the 5' extremity.

After biopanning, it is desirable to learn about the code of the binding members displaying a desired binding specificity. Oligonucleotides of sub-library B remain stably annealed to oligonucleotides of sub-library A, and can work as primers for a DNA polymerase reaction on the template A. The resulting DNA segment, carrying both code A and code B, can be amplified (typically by PCR), using primers which hybridize at the constant extremities of the DNA segment (FIG. 5).

If several specific binding members are isolated at the end of a biopanning experiment, several PCR products will be generated with the process illustrated in FIG. 5. These products will have similar sequences, except for the regions coding for A and B sub-library members. In order to learn more about the relative abundance of the different specific binding members, it will be convenient to create concatenamers, starting from the various PCR products in the reaction mixture. Such concatenated sequences can be "read" by sequencing, revealing both the identity and the frequency of pairs of code A and code B (which uniquely correspond to particular library members).

An alternative decoding strategy is depicted in FIG. 6. Sub-libraries A and B carry chemical moieties at the extremities of partially-annealing oligonucleotides. In most cases, the DNA portion forming a heteroduplex will be constant within the library. Conversely, the other extremities will be designed in a way that heteroduplex formation is disfavored. Such unpaired DNA strands will be available for hybridization with target oligonucleotides (for example, DNA oligonucleotides immobilized on one or more chips). For example, chip A will allow the reading of the identity (and frequency) of members of sub-library A, rescued after a biopanning experiment. Similarly, chip B will allow the reading of the identity (and frequency) of members of sub-library B. A variety of strategies can be considered (e.g., DNA radiolabeling, DNA biotinylation followed by detection with streptavidin-based reagents, etc.) for the visualization of the binding reaction on the chip.

In a first step, the decoding method of FIG. 6 will not provide information about the pairing of code A and code B within specific binding members. However, decoding on chip A and B will suggest candidate components of sub-libraries A and B, to be re-annealed and screened in a successive round of bio-panning. Increasingly stringent binding to the target will be mirrored by a continuous reduction in the number of A and B members, identified on the chip. Ultimately, the possible combinations of the candidate A and B members will be assembled individually (or in smaller pools), and assayed for binding to the target. We refer to this iterative strategy as deconvolution.

Obviously, the decoding method of FIG. 6 is valid also for ESACHEL, when libraries self-assemble to form trimeric or tetrameric complexes (e.g. using DNA triplexes or quadruplexes for the oligomerization of compounds). In these cases, 3 or 4 chips may be used, respectively, which carry distinctive target oligonucleotides for decoding.

If appropriate, the DNA of selected binding moieties of FIG. 6 may be PCR amplified prior to chip hybridization. In this case, oligonucleotide design will resemble the one described in the next paragraph (see also FIG. 7).

Another possible decoding method is illustrated in FIG. 7. Sub-libraries A and B form a heteroduplex, flanked by unique sequences coding for the different library members and by constant DNA segments at the termini. After biopanning, suitable pairs of primers allow the PCR amplification of the two strands, yielding PCR products whose sequence can be identified using standard methods (e.g. by concatenation of the PCR products, followed by subcloning and sequencing. Similar to the chip-based method illustrated in FIG. 6, the method of FIG. 7 will not provide, in general, direct information about pairing of code A and code B in specific binding members. However, (similar to what described for FIG. 6), a deconvolution procedure may be applied (consisting of one or more rounds of panning, followed by sequencing and by the choice of a restricted set of sub-library components for the next ESACHEL screening), restricting the number of candidate ESACHEL members capable of giving specific binders after self-assembly.

Library Construction:

ESACHEL library construction is facilitated not only by the large dimension that can be achieved by self-assembly of sub-libraries, but also by the facile generation and purification of chemical derivatives of DNA oligonucleotides.

As mentioned above, DNA oligonucleotides, bearing a thiol group at their 3' or 5' end, can be purchased from a variety of commercial suppliers. The chemistry of the modification of thiol groups with reagents bearing reactive groups such as iodoacetamido moieties or maleimido moieties is well-established [see for example the molecular Probes catalogue at www.probes.com]. A number of other methodologies may be used in order to chemically couple molecules to oligonucleotides (e.g., use oligonucleotides carrying a primary amino group at their extremity, for the coupling to activated esters). Furthermore, several methods are available in the literature for the chemical modification of 3' or 5' extremities of DNA oligonucleotides, for example during solid phase synthesis procedures.

Chemical derivatives of DNA (or some DNA analogues) have the characteristic property of being highly negatively charged at neutral pH. This facilitates the development of general purification strategies of the DNA derivatives. For example, anion exchange chromatography allows the non-covalent (but stable) immobilization of DNA oligonucleotides (and their derivatives) on a resin, while other components of a reaction mixtures can be washed away. DNA derivatives can then be eluted by buffer change. Alternatively, other purification methods (e.g. reverse phase chromatography, hydrophobic interaction chromatography, hydroxyapatite chromatography etc.) could be considered.

The availability of generally applicable purification procedures for DNA derivatives makes the synthesis of ESACHEL components amenable to robotization [for example using a TECAN Genesys 200-based workstation (TECAN, Männedorf, Switzerland), equipped with liquid handling system and a robotic manipulation arm]. Robotization may be necessary, in order to create ESACHEL sub-libraries containing several hundred different compounds.

The methodologies described in this Patent work not only for small organic molecules, but also for peptides and oligomeric proteins [e.g. antibody Fv fragments, consisting of a VH and VL domain; see Example 1]. Indeed, the attachment of a DNA heteroduplex at the C-terminus of cysteine-tagged VH and VL domains will provide an extra stabilization to the Fv heterodimer.

Biopanning Experiments:

The use of ESACHEL for the identification of specific binders relies on the incubation of ESACHEL components with the target molecule (e.g., a protein of pharmacological interest), followed by the physical separation of the resulting complex from the ESACHEL components which have not bound to the target. In this respect, ESACHEL biopanning experiments are analogous to biopanning experiments which can be performed with phage libraries and/or ribosome display libraries, for which an extensive literature and several experimental protocols are available [Winter, 1994; Viti, 2000; Schaffitzel, 1999]. For example, physical separation of the complex between ESACHEL members and the target molecule, from the pool of non-bound ESACHEL members, could be achieved by immobilizing the target molecule of a solid support (e.g. a plastic tube, a resin, magnetic beads, etc.).

The Chelate Effect:

Some of the contributions of ESACHEL technology for the identification of specific binders are related to a chemical process, termed the "chelate effect". The term chelate was first applied in 1920 by Sir Gilbert T. Morgan and H. D. K. Drew [J. Chem. Soc., 1920, 117, 1456], who stated: "The adjective chelate, derived from the great claw or chela (chely—Greek) of the lobster or other crustaceans, is suggested for the caliper-like groups which function as two associating units and fasten to the central atom so as to produce heterocyclic rings."

The chelate effect can be seen by comparing the reaction of a chelating ligand and a metal ion with the corresponding reaction involving comparable monodentate ligands. For example, comparison of the binding of 2,2'-bipyridine with pyridine or 1,2-diaminoethane (ethylenediamine) with ammonia. It has been known for many years that a comparison of this type always shows that the complex resulting from coordination with the chelating ligand is much more thermodynamically stable.

Let us consider the dissociation steps of a monodentate ligand, compared to multidentate (e.g., bidentate ligands). When a monodentate group is displaced, it is lost into the bulk of the solution. On the other hand, if one end of a bidentate group is displaced the other arm is still attached and it is only a matter of the arm rotating around and it can be reattached again (FIG. 8). In general, the formation of the complex with bidentate groups is favored, compared to the complex with the corresponding monodentate groups.

The chelate effect has been shown to be able to contribute to high-affinity binding not only in the case of multidentate metal ligands, but in many other chemical situations, including binding interactions with macromolecules (e.g., multidentate DNA binding, chelating recombinant antibodies) [Neri D, Momo M, Prospero T, Winter G. High-affinity antigen binding by chelating recombinant antibodies (CRAbs). J Mol. Biol. (1995) 246:367-73].

When examining some ESACHEL embodiments, for example those in which two chemical moieties are oligomerized by means of DNA heteroduplex formation, it is useful to illustrate the chelate effect in the context of the stability of the DNA heteroduplex which bridges the two chemical entities involved in the specific binding interaction with a target. In most cases, it will be convenient to have heteroduplexes (or triplexes or quadruplexes) which de facto do not dissociate in the experimental conditions chosen for the ESACHEL biopanning. Useful information and a discussion on the energetics of cooperative binding with short DNA heteroduplex fragments (8 bp) can be found in Distefano and Dervan, 1993 [Distefano M D, Dervan P B. Energetics of cooperative binding of oligonucleotides with discrete dimerization domains to DNA by triple helix formation Proc Natl Acad Sci USA. (1993) 90: 1179-1183.3.]

Considerations on the Procedures Following ESACHEL Biopanning:

What happens after ESACHEL experiments, when specific binding members have been identified? For some purposes (e.g., certain biochemical experiments), it may be conceivable to use ESACHEL members without further chemical transformations. For example, one may want to measure binding affinities and kinetic constants for the binding of ESACHEL members to a target molecule.

For many applications, however, one may want to covert ESACHEL self-assembled molecules into analogues, in which the chemical entities responsible for the binding are covalently linked. The length, rigidity, stereoelectronic chemical properties and solubility of the linker will influence the binding affinity and performance of the resulting molecule [Shuker S B, Hajduk P J, Meadows R P, Fesik S W. Discovering High-Affinity Ligands For Proteins—Sar by Nmr. Science (1996) 274:1531-1534] (see also Example 4).

EXAMPLES

Example 1

As mentioned in previous sections, one strength of ESA-CHEL technology is its compatibility with a variety of different chemical moieties, including peptides and globular proteins (e.g., antibody domains).

In this example, we show how a simple embodiment of ESACHEL (FIG. 1), featuring cysteine-tagged antibody variable domains covalently linked to DNA oligonucleotides capable of partial heteroduplex formation, leads to the identification of a pair of variable heavy domain (VH) and variable light domain (VL), which yield a specific antigen binding after heterodimerization.

The genes of the VH and VL domains of the L19 antibody (specific for the ED-B domain of fibronectin (Pini A, Viti F, Santucci A, Carnemolla B, Zardi L, Neri P, Neri D. Design and use of a phage display library. Human antibodies with subnanomolar affinity against a marker of angiogenesis eluted from a two-dimensional gel. J Biol Chem. (1998) 273:21769-21776D), of the HyHEL-10 antibody (specific for hen egg lysozyme (Neri, 1995); please note that an internal EcoRI site had previously been mutagenized without altering the protein sequence) and of other antibodies isolated from the ETH-2 library (Viti, 2000), are PCR amplified using the following pairs of primers, which code for a cysteine residue, appended at the C-terminal extremity of each V domain:

```
L19 and ETH-2:
L19VH_Eco_fo
TTT CAC ACA GAA TTC ATT AAA GAG GAG AAA TTA ACT
ATG GAG GTG CAG CTG TTG GAG TCT (SEQ ID NO: 1)

L19VH_Hind_ba
TCA ATC TGA TTA AGC TTA GTG ATG GTG ATG GTG ATG
ACA TCC ACC ACT CGA GAC GGT GAC CAG GGT
(SEQ ID NO: 2)

L19VL_Eco_fo
TTT CAC ACA GAA TTC ATT AAA GAG GAG AAA TTA ACT
ATG GAA ATT GTG TTG ACG CAG TCT CCA
(SEQ ID NO: 3)

L19VL_Hind_ba
TCA ATC TGA TTA AGC TTA GTG ATG GTG ATG GTG ATG
ACA TCC ACC TTT GAT TTC CAC CTT GGT CCC TTG
(SEQ ID NO: 4)

HyHEL-10:
HH10VH_Eco_fo
TTT CAC ACA GAA TTC ATT AAA GAG GAG AAA TTA ACT
ATG GAG GTG AAG CTG CAG CAG TCT (SEQ ID NO: 5)

HH10VH_Hind_ba
TCA ATC TGA TTA AGC TTA GTG ATG GTG ATG GTG ATG
ACA TCC ACC TGC AGA GAC AGT GAC CAG AGT
(SEQ ID NO: 6)

HH10VL_Eco_fo
TTT CAC ACA GAA TTC ATT AAA GAG GAG AAA TTA ACT
ATG GAT ATT GTG CTA ACT CAG TCT CCA
(SEQ ID NO: 7)

HH10VL_Hind_ba
TCA ATC TGA TTA AGC TTA GTG ATG GTG ATG GTG ATG
ACA TCC ACC TTT TAT TTC CAG CTT GGT CCC CCC
(SEQ ID NO: 8)
```

The resulting PCR products are subcloned, using standard molecular biology procedures, into the EcoRI/HindIII sites of plasmid pQE12 (Qiagen, Germany). The resulting plasmids code for V domains, which carry the following sequence at their C-terminus: -Gly-Gly-Cys-His-His-His-His-His-His (SEQ ID NO:29).

The plasmids, encoding the cysteine-tagged V-domains, are electroporated into E. coli cells (preferentially, in the Origami strain of Novagen, which have a slightly oxidizing cytoplasmic redox potential), expressed and purified, using metal chelate chromatography on NiNTA resin (Qiagen, Germany).

The cysteine-tagged V domains are reduced with 1 mM dithiothreitol solution in PBS (50 mM phosphate buffer+100 mM NaCl, pH=7.4), followed by desalting on a PD-10 column (Amersham-Pharmacia, Dübendorf, Switzerland).

In parallel, different oligonucleotides, carrying a thiol group at the 3' end or at the 5' end, are ordered from a commercial supplier (e.g., Microsynth, Balgach, Switzerland). Individual DNA oligonucleotides with the thiol group at the 3' end are used for coupling to individual VH domains. Individual DNA oligonucleotides with the thiol group at the 5' end are used for coupling to individual VL domains.

Representative sequence types are illustrated below. Please note that oligonucleotides of these families are capable of partial heteroduplex formation:

```
L19:

L19_5SH
5-HS-GGA GCT TCT GAA TTC TGT GTG CTG CAT AAT CGA
CAC GAA TTC CGC AGC-3' (SEQ ID NO: 9)

L19_3SH
5'-TCG CGA GGG GAA TTC GTC ATA TAT CAG CAC ACA
GAA TTC AGA AGC TCC- SH-3' (SEQ ID NO: 10)

HyHEL-10:
HyHel10_5SH
5-HS-GGA GCT TCT GAA TTC TGT GTG CTG CAG TGG CGA
CAC GAA TTC CGC AGC-3' (SEQ ID NO: 11)

HyHel10_3SH
5'-TCG CGA GGG GAA TTC GTC ATA GGG CAG CAC ACA
GAA TTC AGA AGC TCC- SH-3' (SEQ ID NO: 12)

Anti-GST (from ETH-2 library):
GST_5SH
5-HS-GGA GCT TCT GAA TTC TGT GTG CTG CTG AGG CGA
CAC GAA TTC CGC AGC-3' (SEQ ID NO: 13)

GST_3SH
5'-TCG CGA GGG GAA TTC GTC AAG AGG CAG CAC ACA
GAA TTC AGA AGC TCC- SH-3' (SEQ ID NO: 14)
```

In parallel reactions, the purified thiol-containing DNA oligonucleotides are reacted with a molar excess of bismaleimido-hexane (Pierce, Belgium) in PBS+DMSO, following the manufacturer's instructions. The resulting derivatives are purified from unreacted bismaleimido-hexane using anion exchange chromatography, then reacted with slight molar excess of purified VH-cys or VL-cys, respectively, at a domain concentration>0.1 mg/ml. The resulting (V domain)-DNA reaction products are separated from unreacted V-domain by anion exchange chromatography.

An equimolar mixture of (V domain)-DNA derivatives is mixed in PBS, heated at 70 degrees centigrade for 1 minute, then let equilibrate until it reaches room temperature. The resulting mixture of ESACHEL compounds is then incubated with a 0.1 µM solution of biotin-ED-B in PBS at room temperature for 10 minutes (Pini, 1998), then captured on streptavidin-coated magnetic beads and washed extensively according to standard procedures.

The resulting bead preparation is then used as template for two separate PCR reactions, which amplify the (L19_5SH, HyHel10_5SH, GST_5SH) and (L19_3SH, HyHel10_3SH, GST_3SH) oligonucleotides (see above), using oligos:

```
1AB_PCRfo
5'-GGA GCT TCT GAA TTC TGT GTG CTG-3'
(SEQ ID NO: 15)

1APCRba
5'-GCT GCG GAA TTC GTG TCG-3'
(SEQ ID NO: 16)

1B_PCRba
5'-TCG CGA GGG GAA TTC GTC-3'
(SEQ ID NO: 17).
```

The resulting PCR products are digested with EcoR1, ligated to form concatenamers, subcloned into a suitable host plasmid, followed by electroporation in *E. coli* and sequencing. The resulting sequence analysis shows a strong bias towards L19 codes (CAT AAT and ATA TAT) over HyHEL-10 and GST codes, indicating a preferential enrichment of VH(L19)-VL(L19) combinations over the other possible assembly products.

Example 2

In this example, we describe how the ESACHEL embodiment of FIG. 1 can be performed in a practical implementation. The experimental strategy outlined here is also applicable to the embodiments described in FIG. 4, in which DNA triplexes or DNA quadruplexes are used to display chemical entities at the extremity of self-assembling oligonucleotides. Two Sub-Libraries are Constructed as Follows:

A sub-library "A" is created, by coupling n compounds to the 3' extremity of n different DNA oligonucleotides. Among the many different possible implementations, a convenient one is represented by the coupling of iodoacetamido- or maleimido-derivatives of n chemical entities to individual DNA oligonucleotides, which carry a thiol group at the 3' end. The coupling can easily be performed at room temperature in PBS (50 mM phosphate buffer+100 mM NaCl, pH=7.4), by simple mixing of the thiol-bearing oligonucleotide (typical concentration range: 10-100 µM) with a molar excess of iodoacetamido- or maleimido-derivative (typical concentration range: 50-500 µM), followed by chromatographic purification of the DNA-chemical entity adduct. The thiol-containing oligonucleotides can be purchased from commercial suppliers.

Each of them contains a constant sequence portion (e.g., 5'XXXXXCAGCACACAGAATTCAGAAGCTCC-3') (SEQ ID NO:18) capable of heteroduplex formation with members of sub-library B (see below). The DNA sequence portion XXXXX at the 5' end is (at least in part) different in each member of the sub-library A, therefore acting as a code.

Similarly, a sub-library "B" is created, by coupling m compounds to the 5' extremity of m different DNA oligonucleotides. Coupling of iodoacetamido- or maleimido-derivatives of m chemical entities to individual DNA oligonucleotides, which carry a thiol group at the 5' end, is performed similar to what described for sub-library "A". Such oligonucleotides can be purchased from commercial suppliers. Each of them contains a constant sequence portion (e.g., 5'-GGAGCTTCT-GAATTCTGTGTGCTGYYYYY-3') (SEQ ID NO:19) capable of heteroduplex formation with members of sub-library A (see above). The DNA sequence portion YYYYY at the 3' end is (at least in part) different in each member of the sub-library B, therefore acting as a code.

A number of other methodologies may be used in order to chemically couple molecules to oligonucleotides (e.g., use oligonucleotides carrying a primary amino group at their extremity, for the coupling to activated esters).

Assembly of sub-library A members with sub-library B members is carried out by mixing the sub-libraries in PBS, heating the mixture at 70 degrees centigrade for 1 minute (if compatible with the stability of the chemical entities used in sub-library construction), followed by equilibration at room temperature. The resulting ESACHEL library contains n×m members, and can be used in biopanning experiments, followed by decoding of the binding members. Addition of magnesium salts to the solution (e.g., 4 mM $MgCl_2$) may further stabilize the DNA structure.

Example 3

This example illustrates one of the many possible decoding methodologies, for ESACHEL embodiments as described in FIG. 1 and in Example 2.

The decoding strategy, schematically depicted in FIG. 5, is based on the principle that, after biopanning of desired ESACHEL binding specificities, PCR fragments are generated, each of which carries the code of pairs of sub-library members, whose combination was rescued in the biopanning experiment, therefore allowing the identification of the corresponding heterodimerized chemical entities.

Chemical entities of sub-libraries A and B (see also FIG. 1 and Example 2) are coupled, individually, to members of two pools of DNA oligonucleotides with the following properties:

One pool of oligonucleotides carries the chemical entities at the 3'-end (pool A), whereas the other pool carries the chemical entity at the 5'-end (pool B).

A sufficient number of bases at the 5' extremity of oligonucleotides of pool B allow the specific dimerization of any individual member of pool B with any individual member of pool A. Inside this dimerization domain, oligonucleotides from pool B contain a "code" region, which codes for the chemical entity at the 5'-end. Oligonucleotides of pool A contain a sufficient number of desoxyribose backbone elements without bases (d-Spacer), to prevent any undesired pairing to the bases of code B.

Oligonucleotides of sub-library A have their distinctive code towards the 5' extremity.

Oligonucleotides of sub-library B remain stably annealed to oligonucleotides of sub-library A, and can work as primers for a DNA polymerase reaction on the template A. The resulting DNA segment, carrying both code A and code B, can be amplified (typically by PCR), using primers which hybridize at the constant extremities of the DNA segment (FIG. 5).

As an example of model oligonucleotides A and B which can be used for the generation of a PCR product, which carries both code A and B, is provided below:

```
typeB_oligo
Chemical entity B-5'-GCA TAC CGG AAT TCC CAG CAT
AAT GAT CGC TAT CGC TGC-3' (SEQ ID NO: 20)

typeA_oligo (D = d-Spacer element)
5'-CGT CAG CTC GAA TTC TCC ATA TAT GCA GCG ATA
GCG ATC DDD DDD CTG GGA ATT CCG GTA TGC-3'-
chemical entity A (SEQ ID NOS: 21 and 30)

CodeABfo
5'-GCA TAC CGG AAT TCC CAG-3' (SEQ ID NO: 22)

CodeABba
5'-CGT CAG CTC GAA TTC TCC-3' (SEQ ID NO: 23)
```

TypeA_oligo and type_B oligo are mixed in approx. equimolar amounts. The resulting mixture is heated up to 70° C., and cooled to room temperature, allowing the heterodimerization of typeA_oligo and type_B oligo. The resulting mixture is mixed with a suitable buffer for PCR reaction, dNTPs (250 μM per nucleotide, Pharmacia). Taq-Polymerase (1U, Appligen) is then added, and followed by incubation of the mixture at 40° C. for 5 minutes. Next, a PCR program with 30 cycles of (90°/1 minute)—(50° C./1 minute)—(72° C./15 seconds) is started after addition of primers CodeABfo and CodeABba (400 μM). After completion of the program, the length of the PCR fragment is checked by standard polyacrylamide gel methodology, using commercial Novex gels. Its sequence identity can be established by digesting the product with EcoRI, followed by cloning into a suitable plasmid and sequencing.

Example 4

Like chelating recombinant antibodies (CRAbs) [Neri, 1995] and small organic ligands identified using SAR by NMR [Shuker, 1996], the high-affinity binding of ESACHEL members to target molecules may rely on the chelate effect.

It is intuitive that the affinity gain contribution of the chelate effect will depend on the length, rigidity, stereoelectronic chemical properties and stability of the linkage between the two (or more) chemical entities, in contact with the target antigen. Furthermore, the affinity gain will directly depend on the magnitude of the association and dissociation rate constants ($k_{on}$ and $k_{off}$) of the individual chemical entities, binding to the target.

In this example, we present a computational model, which provides information about the contribution of the chelate effect, in relation to the above mentioned parameters (linker length, $k_{on}$ and $k_{off}$).

As depicted in FIG. 9, two different chemical entities A and B bind to distinct binding sites of the same target molecule, and are connected by a linker of defined length. It is convenient to define four different states (nI, nII, nIII and nIV), which may interconvert by means of chemical binding equilibria:

nI: Both A and B bound to their binding pocket
nII: A bound to its binding pocket, while B is not bound to its binding pocket
nIII: B bound to its binding pocket, while A is not bound to its binding pocket
nIV: Both A and B not bound to their binding pockets The kinetic parameters $k_{onA}$, $k_{offA}$, $k_{onB}$ and $k_{offB}$, describing the binding properties of the individual chemical entities A and B to the corresponding binding pockets, are known. From these constants, it is possible to determine probabilities for a bound molecule to go off the binding pocket (poff), and for an unbound molecule to bind to its binding pocket (pon) in a defined time increment:

$$poff = k_{off} \cdot \Delta t \quad [1]$$

In first order kinetics, the half life of binding can be expressed as:

$$\tau^{on} = \frac{\ln 2}{k_{on} \cdot [B]} \quad [2]$$

If at time t=0 all molecules B are not bound to the corresponding binding pocket (and if one neglects in a first approximation dissociation processes), the fraction of bound molecules after the time increment Δt can be expressed as follows:

$$\frac{N(\Delta t)}{N(t=0)} = e^{-\Delta t \cdot k_{on} \cdot [B]} \quad [3]$$

If one chooses a sufficiently large ensemble of molecules, the equation [3] can be approximated to the probability that a molecule B binds to its pocket in the time increment Δt.

The equations written so far correspond to chemical entities A and B, which bind to the corresponding pockets independent from one another. Let us assume, however, that A and B are connected by a linker, and that moiety A is bound to its target. It is convenient to express the concentration of B in the vicinity of its target binding pocket as effective concentration, ec.:

$$pon = e^{-\Delta t \cdot k_{on} \cdot ec} \quad [4]$$

In our model, the contribution of the chelate effect to the binding properties of the A-B bidentate molecule to the target is due to an increase of the effective concentration of one of the two binding moieties, when the other one is bound to its binding pocket (FIG. 9). In a simple model, let us assume that, if binding molecule A is bound, the molecule B can be situated with equal likelihood in every position in a half spherical space around molecule A, whereby the radius "rad" (measured in meters) is equal to the linker length. Sterical constraints of the linker, repulsion effects etc. are neglected in this simple model. The same assumption is used when molecule B is bound, and A is unbound.

As a result, the molar effective concentration ec can be computed as:

$$ec = \frac{1}{\left[\frac{1}{2} \cdot \left(\frac{4}{3} \cdot \pi \cdot rad^3\right) \cdot 6.01 \cdot 10^{26}\right]} \quad [5]$$

Based on these assumptions, we designed a computer program to estimate the contribution of the chelate effect to the residual half life of a bidentate binding molecule A-B, where the two individual moieties A and B binding to two distinct binding pockets on the same target molecule are connected with a liker of the length rad. The possibility of A and B binding to two different target molecules is neglected.

In a population of n A-B molecules, the four states of FIG. 9 can be populated by the individual molecules, and it is conceivable that individual molecules are found in different states at different times of observation. In our model, we determined the probabilities "pon" and "poff" of the individual molecules A and B to change their state within a time increment Δt.

As a practical example, let us consider that at time t=0, all molecules A-B are in state nI (both A and B are bound). At every time increment Δt (which is 1 second in the program) the probabilities of the moieties A and B to change their binding status give rise to a new distribution of molecules A-B in the four different states. In the simulation, irreversible dissociation conditions are used (i.e., dissociated molecules A-B, in state nIV are not allowed to bind back to the target). The program repeats these calculations time increment after time increment, until the population of molecules A-B bound to the target (sum of nI, nII and nIII) drops to half of the starting population. The sum of the time increments gives an estimate of the half-life of a bound molecule A-B to its target.

By varying either the initial configuration of the ensemble of molecules, or the parameters $k_{offA}$, $k_{offB}$, $k_{onA}$, $k_{onB}$ and rad, one can estimate the contribution to the chelate effect of different linked chemical entities, in terms of the kinetic stabilization of the complex.

The Code of the Corresponding CHELATE Program (Written in PASCAL) is Listed Below:

```
***************
program chelate;
var
    n, n0 , koffA, koffB, koffAB, konA, konB :double;
    t12A, t12B, t12AB, rad, conc: double;
    linkerA : integer;
    nI, nII, nIII, nIV, deltaI, deltaII, deltaIII, deltaIV : double;
    pAoff, pAon, pBoff, pBon : double;
begin
    writeln;
    writeln ('molecules A and B are connected with a linker ');
    writeln;
    writeln ('koffA [s-1] = ');          (* type in values *)
    readln (koffA);
    writeln ('konA [M-1s-1] = ');
    readln (konA);
    writeln ('koffB [s-1] = ');
    readln (koffB);
    writeln ('konB [s-1] = ');
    readln (konB);
    writeln;
    writeln ('linker length [A] =');
    readln (linkerA);
    t12A:=ln(2)/koffA;   (* calculate t12 and concentration *)
    t12B:=ln(2)/koffB;
    rad:=linkerA*1e-10;
    conc:=1/((2/3*Pi*rad*rad*rad)*6.01e26);
    writeln ('koffA=',koffA, ' t12A=',t12A,' konA=',konA);
    writeln ('koffB=',koffB, ' t12B=',t12B,' konB=',konB);
    writeln ('linker length [m]=',rad);
    writeln ('effective concentration [M]=',conc);
    writeln;
    t12AB:=0;                     (* Parameters *)
    n0:=1e10;
    nI:=n0; nII:=0; nIII:=0; nIV:=0;   (*in this embodiment of the
program, only the nI state is populated at time 0 *)
    n:=nI + nII + nIII;
    pAoff:=koffA;
    pAon:=1-exp(-1*konA*conc);
    pBoff:=koffB;
    pBon:=1-exp(-1*konB*conc);
    while n>n0/2 do
        begin
        deltaI:=0; deltaII:=0; deltaIII:=0; deltaIV:=0;
        t12AB:=t12AB+1;   (* one loop equals one second *)
        (* nI *)
        deltaIV :=deltaIV +(nI*pAoff*pBoff);
        deltaIII:=deltaIII+(nI*pAoff*(1-pBoff));
        deltaII :=deltaII +(nI*(1-pAoff)*pBoff);
        deltaI :=deltaI -(nI*pAoff*pBoff);
        deltaI :=deltaI -(nI*pAoff*(1-pBoff));
        deltaI :=deltaI -(nI*(1-pAoff)*pBoff);
        (* nII *)
        deltaIII:=deltaIII+(nII*pAoff*pBon);
        deltaIV :=deltaIV +(nII*pAoff*(1-pBon));
        deltaI :=deltaI +(nII*(1-pAoff)*pBon);
        deltaII :=deltaII -(nII*pAoff*pBon);
        deltaII :=deltaII -(nII*pAoff*(1-pBon));
        deltaII :=deltaII -(nII*(1-pAoff)*pBon);
        (* nIII *)
        deltaII :=deltaII +(nIII*pAon*pBoff);
        deltaI :=deltaI +(nIII*pAon*(1-pBoff));
        deltaIV :=deltaIV +(nIII*(1-pAon)*pBoff);
        deltaIII:=deltaIII-(nIII*pAon*pBoff);
        deltaIII:=deltaIII-(nIII*pAon*(1-pBoff));
        deltaIII:=deltaIII-(nIII*(1-pAon)*pBoff);
        nI :=nI + deltaI;
        nII :=nII + deltaII;
        nIII:=nIII + deltaIII;
        nIV :=nIV + deltaIV;
        n:=nI+nII+nIII;
        (* nIV is removed from the remaining population *)
        writeln (n,' ',t12AB);
        end;
    writeln;
    writeln ('koffA=',koffA, ' t12A=',t12A,' konA=',konA);
    writeln ('koffB=',koffB, ' t12B=',t12B,' konB=',konB);
    writeln ('linker length [m]=',rad);
    writeln ('effective concentration [M]=',conc);
    writeln;
    writeln ('t12AB=',t12AB,' s');
    writeln;
    readln;
end.
***************
```

Example 5

In many cases, it may be desirable to improve the affinity of an existing binder towards a target molecule (e.g. a pharmaceutical target). Towards, this goal, ESACHEL technology can be used as follows, i.e. omitting the "code" oligonucleotide sequence from the binder to be optimized. Let us suppose that the chemical moiety p binds to a target molecule (e.g., a protein) with an insufficient affinity. It will be convenient to link p to one extremity (e.g., the 5' end) of a suitable oligonucleotide, capable of self-assembly with other oligonucleotide derivatives (typically, by heteroduplex formation, as depicted in FIG. 10).

For example, the chemical moiety p will be coupled to the 5' end of oligonucleotide 5'-GGA GCT TCT GAA TTC TGT GTG CTG-3' (SEQ ID NO:15). It will then be convenient to chemically couple, in individual reactions, many different chemical moieties q at the 3' end of oligonucleotides, of general sequence 5'-XX . . . XX-Y-CAG CAC ACA GAA TTC AGA AGC TCC-3' (SEQ ID NO:24), whereas:

the XX . . . XX portion will be different for the different compounds;

Y represents a biotinylated base analogue;

the sequence 5'-CAG CAC ACA GAA TTC AGA AGC TCC-3' (SEQ ID NO:31) will be identical in all cases, allowing the heteroduplex formation with the sequence 5'-GGA GCT TCT GAA TTC TGT GTG CTG -3' (SEQ ID NO:15), chemically coupled to p, for all members of the ensemble of molecules q.

The resulting library will pair p with molecules q, each of which bears a distinctive oligonucleotide code. The self-assembled library can be submitted to biopanning, under conditions of suitable stringency. The binders rescued at the end of the biopanning procedure will be identified by means of their code. For example, the codes of the molecules q, which together with p give rise to high-affinity binders for the target molecule, can be read by hybridization to an oligonucleotide chip, in which the different positions are covered with oligonucleotides, which are complementary to the sequences XX . . . XX of the members of the sub-library Q. The biotin moiety on members of sub-library Q will allow the detection of the binding events on the chip.

Candidate chemical moieties q will then be chemically linked to p, and the resulting conjugate will be used as a specific binder for the target molecule of interest.

Example 6

Model Selection of Modified DNA-Fragments for Binding to Streptavidin

In order to show that multivalent binding molecules in ESACHEL format are preferentially captured by a target protein with multiple binding sites, we performed model selection experiments with DNA heteroduplex, modified in ESACHEL format with iminobiotin and/or a fluorescent molecule (Cy5), using streptavidin-coated sepharose beads as capture reagent. Iminobiotin is an analogue of biotin, which displays a substantially reduced affinity to streptaviding [Green (1966), *Biochem. J.* 101, 774-780]. In turn, streptavidin is a stable homotetrameric protein, with four binding sites for (imino)biotin. These sites can be classified into two pairs of adjacent binding sites (see FIG. 11).

We purchased from IBA (Göttingen, Germany) the following oligonucleotides, modified at their 3' or 5' extremity with iminobiotin or Cy5:

```
1.) iminobiotinyl-NH-(CH2)6-5'-GGA GCT TCT GAA TTC
    TGT GTG CTG ATT GGC CGA CAC GAA TTC CGC AGC-3'
    (SEQ ID NO: 25)

2.) 5'-TCG CGA GGG GAA TTC GTC ATT TAC CAG CAC
    ACA GAA TTC AGA AGC TCC-3'-(CH2)6-NH-
    iminobiotinyl (SEQ ID NO: 26)

3.) CY5-NH-(CH2)6-5'-GGA GCT TCT GAA TTC TGT GTG
    CTG GTG TGC CGA CAC GAA TTC CGC AGC-3'
    (SEQ ID NO: 27)

4.) 5'-TCG CGA GGG GAA TTC GTC GTT AAG CAG CAC
    ACA GAA TTC AGA AGC TCC-3'-(CH2)6-NH-CY5
    (SEQ ID NO: 28)
```

Both iminobiotin and Cy5 were coupled to amino-tagged oligonucleotide by formation of an amide bond.

The oligonucleotides 2.) and 4.) were radiolabeled with 33P in separate, parallel reactions, using Redivue gamma $^{33}$P ATP (amersham pharmacia, Uppsala, Sweden) and T4 Polynucleotide Kinase (USB Corporation, Cleveland, UàSA). In one radiolabelling reaction, 350 picomoles of the oligonucleotide were mixed with 5 µL (5 U/µL) T4 Polynucleotide Kinase, 1 µL (10 µCi/µL) Redivue gamma $^{33}$P ATP and 5 µL (10×) T4 Polynucleotide Kinase buffer in a total volume of 50 µL. After 30 minutes incubation at 37° C., the reaction was terminated by a 5 minute denaturation step at 65° C. The oligonucleotides were separated from unreacted gamma $^{33}$P ATP by purification with the Nucleotide Removal Kit (Qiagen, Hilden, Germany), using 200 µL of 10 mM Tris-Cl as eluting buffer.

Compounds 1-4 were annealed with each other in the following combinations, yielding the modified DNA fragments 5-8 (see FIG. 12):

5=1+2

6=1+4

7=3+2

8=3+4

10 µL of each oligonucleotide were mixed in a total volume of 150 µL, using 15 µL 100 mM $Na_2CO_3$ 500 mM NaCl pH10 as buffer. Addition of magnesium salts increase the stability of DNA and ESACHEL performance. The oligonucleotide mixtures were incubated 5 minutes at 70° C., following another 5 minutes at 50° C., allowing annealing of the DNA strands.

In parallel experiments, 33P-labeled compounds 5-8 mixed with 50 µl of streptavidin sepharose (amersham pharmacia, Uppsala, Sweden). The resulting slurries were incubated at room temperature for 30 minutes, and washed up to 5 times by centrifugating the tubes for 15 seconds at 6000 rpm in a tabletop centrifuge, aspirating off the supernatant, and redissolving the beads in 500 µL 10 mM $Na_2CO_3$ 50 mM NaCl pH10. After the washing steps, the iminobiotinylated oligonucleotides were eluted from streptavidin with 500 µL 50 mM ammonium acetate 50 mM NaCl, pH 4.0, exploiting the pH-dependency of iminobiotin binding to streptavisdin. 33P decays from aliquots taken from the different steps of the selection procedure were determined using a Beckman LS6500 scintillation counter (GMI, Albertville, USA).

The relative enrichment factors recovered after the elution step for compounds 5-8 (normalized relative to the recovery of radioactivity for the DNA fragment 8, carrying two Cy5 moieties) is demonstrated in FIG. 12. The results show that, even in this non-optimized selection experiment, the bidendate ligand in ESACHEL format is preferentially enriched, compared to ESACHEL compounds carrying a single streptavidin ligand or no streptavidin ligand at all.

Example 7

4-sulfonamido benzamides retain binding affinity towards human carbonic anhydrase after covalent coupling to an oligonucleotides Many binding molecules, specific for human carbonic anhydrase, are known [Zollner (1999), *Handbook of Enzyme Inhibitors, 3rd Edition*]. Sulfonamido benzoic acid derived compounds, in particular, have affinity for carbonic anhydrase in the micromolar range, and lend themselves to ESACHEL affinity maturation procedures.

We measured the inhibitory concentration 50 [IC50] of 4-sulfonamido benzoic acid propylamide using an activity assay described by Pocker and Stone [(1967), *Biochemistry* 6, 668-678]. In short, we incubated carbonic anhydrase in separate wells of a transparent 96 well microtiter plate with different concentrations of the inhibitor and the substrate 4-Nitrophenylacetate. The proceeding of the reaction was monitored at the increase of absorption at 400 nm due to formation of the product 4-nitrophenol.

The results of this experiment are plotted in FIG. 13, and show that 4-sulfonamido benzoic acid propylamide has an IC50 of 6 µM towards human carbonic anhydrase.

In order to demonstrate that coupling of 4-sulfonamido benzoic acid derivatives to DNA maintain the binding affinity of this pharmacophore to carbonic anhydrase (an essential pre-requisite for ESACHEL implementation), we coupled 4-sulfonamido benzyl chloride to the amino-tagged oligonucleotide $NH_2$—$(CH_2)_6$-5'-AGAGC-3', purchased from IBA (Göttingen, Germany).

The resulting sulfonamide was purified by HPLC on a reverse phase C18 column [Vydac, Hesperia, USA], yielding a pure product with the expected MALDI-TOF mass spectrum. This compound retained a binding affinity towards carbonic anhydrase comparable to the one of the 4-sulfonamido benzoic acid propylamide.

Double-stranded DNA derivatives, in which one strand is chemically modified with 4-sulfonamido benzylamide, while the other (partially complementary) strands carry a variety of different chemical moieties and bear a characteristic DNA code, represent the basis for the affinity maturation of 4-sulfonamido benzoic acid propylamide, to yield high-affinity bidentate ligands to carbonic anhydrase.

What is claimed is:

1. A chemical library comprising stable combination reaction products between a first number of chemical compounds of a sub-library A with a sub-library B of chemical compounds, wherein the compounds of the sub-library A comprise:
   (i) a chemical moiety (p) capable of performing a binding interaction with a single target molecule, and
   (ii) an oligonucleotide (b) or functional analogue thereof, which comprises a variable, unique distinctive sequence tag (b2) coding for the identification of the chemical moiety (p) of its compound and a common self-assembly sequence (b1) capable of performing a combination reaction and of building a stable combination reaction product with a common self-assembly sequence (b1') of a plurality of chemical compounds of the sub-library B, wherein the sub-library B comprises a second number of chemical compounds each comprising:
   (i) a chemical moiety (q) capable of performing a binding interaction with a single target molecule, and
   (ii) an oligonucleotide (b') or functional analogue thereof, which comprises a variable, unique distinctive sequence tag (b2') coding for the identification of the chemical moiety (q) of its compound, and the common self-assembly sequence (b 1'),
   wherein the chemical moieties (p,q) are peptides or globular proteins.

2. The chemical library of claim 1, wherein the chemical compounds of sub-library A and sub-library B are capable to form stable combination reaction products in the absence of said target molecule(s).

3. The chemical library of claim 1, wherein sub-library A and sub-library B each comprise at least four chemical compounds.

4. The chemical library of claim 1, wherein the chemical compounds of each sub-library comprise a different chemical moiety (p,q) than other members of the respective sub-library.

5. The chemical library of claim 1, wherein the chemical moieties (p) of sub-library A are coupled to a 3' extremity of the oligonucleotide (b1), and wherein the chemical moieties (q) of sub-library B are coupled to a 5' extremity of the oligonucleotide (b1').

6. The chemical library of claim 1, wherein said stable combination reaction products are derived by forming oligomers selected from the group comprising dimers, trimers, and tetramers, by hetero-oligomerization of the self-assembly sequences (b1,b1') of the oligonucleotides (b,b'), thereby forming heteroduplexes, heterotriplexes or heteroquadruplexes.

7. The chemical library of claim 1, wherein in sub-library A or in sub-library B, iodoacetamido- or maleimido-derivatives of the respective chemical moieties have been coupled to individual DNA oligonucleotides which carry a thiol group at the 3' or 5' extremity.

8. The chemical library of claim 1, wherein in sub-library A or in sub-library B, amide derivatives —forming chemical structures according to the formula —O—P(O)$_2$—O—(CH$_2$)n-NH—CO—R, where R corresponds to a number of different chemical entities, and n ranges between 1 and 10—are coupled to the oligonucleotides carrying a phosphodiester bond at one extremity.

9. The chemical library of claim 1, wherein in sub-library A the self-assembly sequence (b1) is interrupted by a d-spacer, the d-spacer preventing any undesired pairing to the bases of distinctive sequence tag (b2') which encodes sub-library B, and wherein the oligonucleotide (b) of sub-library A has its distinctive sequence tag (b2) towards the 5' extremity.

10. The chemical library of claim 1, wherein each chemical compound of sub-library A further comprises at least one chemical group that is capable of forming a covalent bond with at least one chemical group of a chemical compound of sub-library B with which had been formed a stable combination reaction product.

11. The chemical library of claim 1, wherein in sub-library A, each oligonucleotide (b) or functional analogue thereof is directly and covalently linked to a chemical moiety (p) and wherein in sub-library B, each oligonucleotide (b') of or functional analogue thereof is directly and covalently linked to a chemical moiety (q).

12. The chemical library of claim 1, wherein in the chemical compounds of sub-library A and sub-library B, the respective oligonucleotides (b,b') or functional analogues thereof further each comprise a linking portion which is situated between the respective self-assembly sequences (b1,b1') and the respective chemical moieties (p,q).

13. The chemical library of claim 1, wherein the sequences of the distinctive sequence tags (b2,b2') of each oligonucleotide (b,b') or the functional analogues thereof are situated between their respective chemical moieties (p,q) and their respective self-assembly sequences (b1,b1').

14. The chemical library of claim 1, wherein in the stable combination reaction products between members of a sub-library A with a sub-library B, the respective members in each stable combination reaction product are covalently linked to each other.

15. A chemical compound or sub-library A of chemical compounds, the chemical compound or each chemical compound of said sub-library A comprising:
   (i) a chemical moiety (p) capable of performing a binding interaction with a single target molecule, and
   (ii) an oligonucleotide (b) or functional analogue thereof, both of which comprise a variable, unique distinctive sequence tag (b2) coding for the identification of the chemical moiety (p),
   wherein the chemical compound or each chemical compound of said sub-library A further comprises a common self-assembly sequence (b1) capable of performing a combination reaction and of building, in the absence of said target molecule, a stable combination reaction product with a common self-assembly sequence (b1') of a plurality of chemical compounds of a sub-library B with a chemical moiety (q) and an oligonucleotide (b') or functional analogue thereof, and
   wherein the chemical moieties (p,q) are peptides or globular proteins.

16. The chemical library of claim 1, wherein both chemical moieties (p,q) of the stable combination reaction product of one chemical compound of sub-library A and of one chemical compound of sub-library B bind to the same target molecule.

17. The chemical library of claim 1, wherein the chemical moiety (p) and the chemical moiety (q) are not covalently linked.

* * * * *

SEQUENCE LISTING

<160> NUMBER OF SEQ ID NOS: 31

<210> SEQ ID NO 1
<211> LENGTH: 60
<212> TYPE: DNA
<213> ORGANISM: Artificial Sequence
<220> FEATURE:
<223> OTHER INFORMATION: Synthetic Primer L19VH_Eco_fo

<400> SEQUENCE: 1
tttcacacag aattcattaa agaggagaaa ttaactatgg aggtgcagct gttggagtct    60

<210> SEQ ID NO 2
<211> LENGTH: 66
<212> TYPE: DNA
<213> ORGANISM: Artificial Sequence
<220> FEATURE:
<223> OTHER INFORMATION: Synthetic Primer L19VH_Hind_ba

<400> SEQUENCE: 2
tcaatctgat taagcttagt gatggtgatg gtgatgacat ccaccactcg agacggtgac    60
cagggt                                                               66

<210> SEQ ID NO 3
<211> LENGTH: 63
<212> TYPE: DNA
<213> ORGANISM: Artificial Sequence
<220> FEATURE:
<223> OTHER INFORMATION: Synthetic Primer L19VL_Eco_fo

<400> SEQUENCE: 3
tttcacacag aattcattaa agaggagaaa ttaactatgg aaattgtgtt gacgcagtct    60
cca                                                                  63

<210> SEQ ID NO 4
<211> LENGTH: 69
<212> TYPE: DNA
<213> ORGANISM: Artificial Sequence
<220> FEATURE:
<223> OTHER INFORMATION: Synthetic Primer L19VL_Hind_ba

<400> SEQUENCE: 4
tcaatctgat taagcttagt gatggtgatg gtgatgacat ccacctttga tttccacctt    60
ggtcccttg                                                            69

<210> SEQ ID NO 5
<211> LENGTH: 60
<212> TYPE: DNA
<213> ORGANISM: Artificial Sequence
<220> FEATURE:
<223> OTHER INFORMATION: Synthetic Primer HH10VH_Eco_fo

<400> SEQUENCE: 5
tttcacacag aattcattaa agaggagaaa ttaactatgg aggtgaagct gcagcagtct    60

<210> SEQ ID NO 6
<211> LENGTH: 66
<212> TYPE: DNA
<213> ORGANISM: Artificial Sequence
<220> FEATURE:
<223> OTHER INFORMATION: Synthetic Primer HH10VH_Hind_ba

<400> SEQUENCE: 6

-continued

```
tcaatctgat taagcttagt gatggtgatg gtgatgacat ccacctgcag agacagtgac    60
cagagt                                                              66
```

<210> SEQ ID NO 7
<211> LENGTH: 63
<212> TYPE: DNA
<213> ORGANISM: Artificial Sequence
<220> FEATURE:
<223> OTHER INFORMATION: Synthetic Primer HH10VL_Eco_fo

<400> SEQUENCE: 7

```
tttcacacag aattcattaa agaggagaaa ttaactatgg atattgtgct aactcagtct    60
cca                                                                 63
```

<210> SEQ ID NO 8
<211> LENGTH: 69
<212> TYPE: DNA
<213> ORGANISM: Artificial Sequence
<220> FEATURE:
<223> OTHER INFORMATION: Synthetic Primer HH10VL_Hind_ba

<400> SEQUENCE: 8

```
tcaatctgat taagcttagt gatggtgatg gtgatgacat ccacctttta tttccagctt    60
ggtcccccc                                                           69
```

<210> SEQ ID NO 9
<211> LENGTH: 48
<212> TYPE: DNA
<213> ORGANISM: Artificial Sequence
<220> FEATURE:
<223> OTHER INFORMATION: Synthetic Primer L19_5SH with 5'-thiol
<220> FEATURE:
<221> NAME/KEY: modified_base
<222> LOCATION: (1)..(1)
<223> OTHER INFORMATION: n is g modified by a thiol group

<400> SEQUENCE: 9

```
ngagcttctg aattctgtgt gctgcataat cgacacgaat tccgcagc                48
```

<210> SEQ ID NO 10
<211> LENGTH: 48
<212> TYPE: DNA
<213> ORGANISM: Artificial Sequence
<220> FEATURE:
<223> OTHER INFORMATION: Synthetic Primer L19_3SH with 3'-thiol
<220> FEATURE:
<221> NAME/KEY: modified_base
<222> LOCATION: (48)..(48)
<223> OTHER INFORMATION: n is c modified by a thiol group

<400> SEQUENCE: 10

```
tcgcgagggg aattcgtcat atatcagcac acagaattca gaagctcn                48
```

<210> SEQ ID NO 11
<211> LENGTH: 48
<212> TYPE: DNA
<213> ORGANISM: Artificial Sequence
<220> FEATURE:
<223> OTHER INFORMATION: Synthetic Primer HyHel10_5SH with 5'-thiol
<220> FEATURE:
<221> NAME/KEY: modified_base
<222> LOCATION: (1)..(1)
<223> OTHER INFORMATION: n is g modified by a thiol group

<400> SEQUENCE: 11

```
ngagcttctg aattctgtgt gctgcagtgg cgacacgaat tccgcagc                48
```

```
<210> SEQ ID NO 12
<211> LENGTH: 48
<212> TYPE: DNA
<213> ORGANISM: Artificial Sequence
<220> FEATURE:
<223> OTHER INFORMATION: Synthetic Primer HyHel10_3SH with 3'-thiol
<220> FEATURE:
<221> NAME/KEY: modified_base
<222> LOCATION: (48)..(48)
<223> OTHER INFORMATION: n is c modified by a thiol group

<400> SEQUENCE: 12
tcgcgagggg aattcgtcat agggcagcac acagaattca gaagctcn                48

<210> SEQ ID NO 13
<211> LENGTH: 48
<212> TYPE: DNA
<213> ORGANISM: Artificial Sequence
<220> FEATURE:
<223> OTHER INFORMATION: Synthetic Primer GST_5SH with 5'-thiol
<220> FEATURE:
<221> NAME/KEY: modified_base
<222> LOCATION: (1)..(1)
<223> OTHER INFORMATION: n is g modified by a thiol group

<400> SEQUENCE: 13
ngagcttctg aattctgtgt gctgctgagg cgacacgaat tccgcagc                48

<210> SEQ ID NO 14
<211> LENGTH: 48
<212> TYPE: DNA
<213> ORGANISM: Artificial Sequence
<220> FEATURE:
<223> OTHER INFORMATION: Synthetic Primer GST_3SH with 3'-thiol
<220> FEATURE:
<221> NAME/KEY: modified_base
<222> LOCATION: (48)..(48)
<223> OTHER INFORMATION: n is g modified by a thiol group

<400> SEQUENCE: 14
tcgcgagggg aattcgtcaa gaggcagcac acagaattca gaagctcn                48

<210> SEQ ID NO 15
<211> LENGTH: 24
<212> TYPE: DNA
<213> ORGANISM: Artificial Sequence
<220> FEATURE:
<223> OTHER INFORMATION: Synthetic Primer 1AB_PCRfo

<400> SEQUENCE: 15
ggagcttctg aattctgtgt gctg                                          24

<210> SEQ ID NO 16
<211> LENGTH: 18
<212> TYPE: DNA
<213> ORGANISM: Artificial Sequence
<220> FEATURE:
<223> OTHER INFORMATION: Synthetic Primer 1APCRba

<400> SEQUENCE: 16
gctgcggaat tcgtgtcg                                                 18

<210> SEQ ID NO 17
<211> LENGTH: 18
<212> TYPE: DNA
<213> ORGANISM: Artificial Sequence
<220> FEATURE:
<223> OTHER INFORMATION: Synthetic Primer 1B_PCRba
```

```
<400> SEQUENCE: 17
tcgcgagggg aattcgtc                                                          18

<210> SEQ ID NO 18
<211> LENGTH: 29
<212> TYPE: DNA
<213> ORGANISM: Artificial Sequence
<220> FEATURE:
<223> OTHER INFORMATION: Synthetic Primer with 5' sequence acting as a
      code for sub-library A
<220> FEATURE:
<221> NAME/KEY: misc_feature
<222> LOCATION: (1)..(5)
<223> OTHER INFORMATION: n is a, c, g, or t

<400> SEQUENCE: 18
nnnnncagca cacagaattc agaagctcc                                              29

<210> SEQ ID NO 19
<211> LENGTH: 29
<212> TYPE: DNA
<213> ORGANISM: Artificial Sequence
<220> FEATURE:
<223> OTHER INFORMATION: Synthetic Primer with 3' sequence acting as a
      code for sub-library B
<220> FEATURE:
<221> NAME/KEY: misc_feature
<222> LOCATION: (25)..(29)
<223> OTHER INFORMATION: n is a, c, g, or t

<400> SEQUENCE: 19
ggagcttctg aattctgtgt gctgnnnnn                                              29

<210> SEQ ID NO 20
<211> LENGTH: 39
<212> TYPE: DNA
<213> ORGANISM: Artificial Sequence
<220> FEATURE:
<223> OTHER INFORMATION: Synthetic Primer typeB_oligo

<400> SEQUENCE: 20
gcataccgga attcccagca taatgatcgc tatcgctgc                                   39

<210> SEQ ID NO 21
<211> LENGTH: 39
<212> TYPE: DNA
<213> ORGANISM: Artificial Sequence
<220> FEATURE:
<223> OTHER INFORMATION: Synthetic 5' end of Primer typeA_oligo with
      spacer element
<220> FEATURE:
<221> NAME/KEY: modified_base
<222> LOCATION: (39)..(39)
<223> OTHER INFORMATION: n is c modified through a 3' phosphodiester
      bond by 6 abasic nucleotides linked through a phosphodiester bond
      to the 5' end of SEQ ID NO:30

<400> SEQUENCE: 21
cgtcagctcg aattctccat atatgcagcg atagcgatn                                   39

<210> SEQ ID NO 22
<211> LENGTH: 18
<212> TYPE: DNA
<213> ORGANISM: Artificial Sequence
<220> FEATURE:
<223> OTHER INFORMATION: Synthetic Primer CodeABfo

<400> SEQUENCE: 22
gcataccgga attcccag                                                          18
```

```
<210> SEQ ID NO 23
<211> LENGTH: 18
<212> TYPE: DNA
<213> ORGANISM: Artificial Sequence
<220> FEATURE:
<223> OTHER INFORMATION: Synthetic Primer CodeABba

<400> SEQUENCE: 23
cgtcagctcg aattctcc                                                       18

<210> SEQ ID NO 24
<211> LENGTH: 24
<212> TYPE: DNA
<213> ORGANISM: Artificial Sequence
<220> FEATURE:
<223> OTHER INFORMATION: Synthetic Primer linked to primer by a
      biotinylated base analog with 5' sequence specific for a chemical
      moiety
<220> FEATURE:
<221> NAME/KEY: modified_base
<222> LOCATION: (1)..(1)
<223> OTHER INFORMATION: n is c modified by a biotinylated base analog

<400> SEQUENCE: 24
nagcacacag aattcagaag ctcc                                                24

<210> SEQ ID NO 25
<211> LENGTH: 48
<212> TYPE: DNA
<213> ORGANISM: Artificial Sequence
<220> FEATURE:
<223> OTHER INFORMATION: Synthetic Primer coupled to 5' iminobiotinyl-
      NH-(CH2)6 group
<220> FEATURE:
<221> NAME/KEY: modified_base
<222> LOCATION: (1)..(1)
<223> OTHER INFORMATION: n is g modified by an iminobiotinyl-NH-(CH2)6
      group

<400> SEQUENCE: 25
ngagcttctg aattctgtgt gctgattggc cgacacgaat tccgcagc                      48

<210> SEQ ID NO 26
<211> LENGTH: 48
<212> TYPE: DNA
<213> ORGANISM: Artificial Sequence
<220> FEATURE:
<223> OTHER INFORMATION: Synthetic Primer coupled to 3' iminobiotinyl-
      NH-(CH2)6 group
<220> FEATURE:
<221> NAME/KEY: modified_base
<222> LOCATION: (48)..(48)
<223> OTHER INFORMATION: n is c modified by an iminobiotinyl-NH-(CH2)6
      group

<400> SEQUENCE: 26
tcgcgagggg aattcgtcat ttaccagcac acagaattca gaagctcn                      48

<210> SEQ ID NO 27
<211> LENGTH: 48
<212> TYPE: DNA
<213> ORGANISM: Artificial Sequence
<220> FEATURE:
<223> OTHER INFORMATION: Synthetic Primer coupled to 5' CY5-NH-(CH2)6
      group
<220> FEATURE:
<221> NAME/KEY: modified_base
<222> LOCATION: (1)..(1)
<223> OTHER INFORMATION: n is g modified by an CY5-NH-(CH2)6 group
```

```
<400> SEQUENCE: 27
ngagcttctg aattctgtgt gctggtgtgc cgacacgaat tccgcagc                        48

<210> SEQ ID NO 28
<211> LENGTH: 48
<212> TYPE: DNA
<213> ORGANISM: Artificial Sequence
<220> FEATURE:
<223> OTHER INFORMATION: Synthetic Primer coupled to 3' CY5-NH-(CH2)6
      group
<220> FEATURE:
<221> NAME/KEY: modified_base
<222> LOCATION: (48)..(48)
<223> OTHER INFORMATION: n is c modified by a CY5-NH-(CH2)6 group

<400> SEQUENCE: 28
tcgcgagggg aattcgtcgt taagcagcac acagaattca gaagctcn                        48

<210> SEQ ID NO 29
<211> LENGTH: 9
<212> TYPE: PRT
<213> ORGANISM: Artificial Sequence
<220> FEATURE:
<223> OTHER INFORMATION: Synthetic sequence at the C-terminus of
      products subcloned into pQE12

<400> SEQUENCE: 29

Gly Gly Cys His His His His His His
1               5

<210> SEQ ID NO 30
<211> LENGTH: 18
<212> TYPE: DNA
<213> ORGANISM: Artificial Sequence
<220> FEATURE:
<223> OTHER INFORMATION: Synthetic 3' end of Primer typeA_oligo with
      spacer element
<220> FEATURE:
<221> NAME/KEY: modified_base
<222> LOCATION: (1)..(1)
<223> OTHER INFORMATION: n is c modified through a 5' phosphodiester
      bond by 6 abasic nucleotides linked through a phosphodiester bond
      to the 3' end of SEQ ID NO:21

<400> SEQUENCE: 30
ntgggaattc cggtatgc                                                         18

<210> SEQ ID NO 31
<211> LENGTH: 24
<212> TYPE: DNA
<213> ORGANISM: Artificial Sequence
<220> FEATURE:
<223> OTHER INFORMATION: Synthetic Primer linked to primer by a
      biotinylated base analog with 5' sequence specific for a chemical
      moiety

<400> SEQUENCE: 31
cagcacacag aattcagaag ctcc                                                  24
```